(12) United States Patent
Fewell et al.

(10) Patent No.: US 8,623,837 B2
(45) Date of Patent: Jan. 7, 2014

(54) COMBINATION OF IMMUNO GENE THERAPY AND CHEMOTHERAPY FOR TREATMENT OF CANCER AND HYPERPROLIFERATIVE DISEASES

(75) Inventors: Jason G. Fewell, Madison, AL (US); Majed Matar, Madison, AL (US); Jennifer Rice, Grant, AL (US); Danny H. Lewis, Hartselle, AL (US); Khursheed Anwer, Madison, AL (US)

(73) Assignee: Egen, Inc., Huntsville, AL (US)

( * ) Notice: Subject to any disclaimer, the term of this patent is extended or adjusted under 35 U.S.C. 154(b) by 57 days.

(21) Appl. No.: 13/109,473

(22) Filed: May 17, 2011

(65) Prior Publication Data

US 2011/0218231 A1  Sep. 8, 2011

Related U.S. Application Data

(63) Continuation of application No. 11/261,931, filed on Oct. 28, 2005, now Pat. No. 7,964,571.

(60) Provisional application No. 60/635,042, filed on Dec. 9, 2004.

(51) Int. Cl.
*A61K 48/00* (2006.01)
*C12N 15/00* (2006.01)
*C12N 15/82* (2006.01)

(52) U.S. Cl.
USPC ........ 514/44 R; 435/320.1; 435/468; 435/455

(58) Field of Classification Search
USPC ...................... 514/44 R; 435/320.1, 468, 455
See application file for complete search history.

(56) References Cited

U.S. PATENT DOCUMENTS

| | | | |
|---|---|---|---|
| 6,696,038 | B1 | 2/2004 | Mahato et al. |
| 7,964,571 | B2 | 6/2011 | Fewell |
| 2003/0018002 | A1 | 1/2003 | Sagara |
| 2004/0142474 | A1 | 7/2004 | Mahato et al. |

FOREIGN PATENT DOCUMENTS

| | | |
|---|---|---|
| WO | 01/91789 | 6/2001 |
| WO | 02/22174 | 3/2002 |
| WO | 03/008555 | 1/2003 |

OTHER PUBLICATIONS

Merdan et al., "Pegylated polyethylenimine-Fab' antibody fragment conjugates for targeted gene delivery to human ovarian carcinoma cells", Bioconjug. Chem., vol. 14, pp. 989-996 (2003).
Chiu et al., "Tumor-targeted gene delivery via anti-HER2 antibody (trastuzumab, Herceptin) conjugated polyethylenimine", J. Control Release, vol. 97, pp. 357-369 (2004).
Aigner et al., "Delivery of unmodified bioactive ribozymes by an RNA-stabilizing polyethylenimine (LMWW-PEI) efficiently downregulates gene expression", Gene Ther., vol. 9, pp. 1700-1707 (2002).
Daqing et al., "Combination Nonviral Interleukin 2 and Interleukin 12 Gene Therapy for Head and Neck Squamous Cell Carcinoma", Arch. Otolaryngol. Head Neck Surg., vol. 127, pp. 1319-1324 (2001).
Anwer et al., "Cationic Lipid-based Delivery System for Systemic Cancer Gene Therapy", Cancer Gene Ther., vol. 7, pp. 1156-1164 (2000).
Zagozdzon et al., "The Potentiated Antileukemic Effects of Doxorubicin and Interleukin-12 Combination are Not Dependant on Nitric Oxide Production", Cancer Lett., vol. 147, pp. 67-75 (1999).
Daqing et al., "Interleukin 2 Gene Transfer Prevents NKG2D Suppression and Enhances Antitumor Efficacy in Combination with Cisplatin for Head and Neck Squamous Cell Cancer", Cancer Res., vol. 62, pp. 4023-4028 (2002).
Teicher et al., "Optimal Scheduling of Interleukin 12 and Chemotherapy in the Murine MB-49 Bladder Carcinoma and B16 Melonoma", Clin. Cancer Res., vol. 3, pp. 1661-1667 (1997).
Lenzi et al., "Phase I Study of Intraperitoneal Recombinant Human Interleukin 12 in Patients with Mullerian Carcinoma, Gastrointestinal Primary Malignanceis, and Mesothelioma", Clin. Cancer Res., vol. 8, pp. 3686-3695 (2002).
Davis, "Non-Viral Gene Delivery Systems", Curr. Opin. Biotechnol., vol. 13, pp. 128-131 (2002).
Wei et al., "Sustained Gene Expression in Transplanted Skin Fibroblasts in Rats", Gene Ther., vol. 6, pp. 840-844 (1999).
Schuh et al., "DNA-Based Vaccine Against La Crosse Virus: Protective Immune Response Mediated by Neutralizing Antibodies and CD4+T Cells", Gene Ther., vol. 10, pp. 1649-1658 (1999).
Mendiratta et al., "Combination of Interleukin 12 and Interferon a Gene Therapy Inducces a Synergistic Antitumor Response against Colon and Renal Cell Carcinoma", Gene Ther., vol. 11, pp. 1851-1862 (2000).
Lesage et al., "Evaluation and optimization of DNA delivery into gliosarcoma 9L cells by a cholesterol-based cationic liposome", Biochimica et Biophysica Acta 1564:393-402 (2002).
Dow et al., "Intravenous Cytokine Gene Delivery by Lipid-DNA Complexes Controls the Growth of Established Lung Metastases", Human Gene Therapy, 10:2961-2972 (1999).
Liu et al., "Cationic Liposome-mediated Intravenous Gene Delivery", The Journal of Biological Chemistry, 270 (42):24864-24870 (1995).
Carrion et al., "Preparation of longOcirculating immunoliposomes using PEG-cholesterol conjugates: effect of the spacer arm between PEG and cholesterol on liposomal characteristics", Chemistry and Physics of Lipids, 113:97-110 (2001).
Lee et al., "Intraperitoneal gene delivery mediated by a novel cationic liposome in a peritoneal disseminated ovarian cancer model", Gene Therapy, 9:859-866 (2002).
Hong et al., "Stablization of cationic liposome-plasmid DNA complexes by polyamines and poly(ethylene glycol)—phospholipid conjugates for efficient in vivo gene delivery", FEBS Letters 400:233-237 (1997).
Fidler, "Orthotopic implantation of human colon carcinomas into nude mice provides a valuable model for the biology and therapy of metastasis", Cancer and Metastasis Reviews, 10:229-243 (1991).

(Continued)

*Primary Examiner* — Marcia S. Noble
*Assistant Examiner* — Magdalene Sgagias
(74) *Attorney, Agent, or Firm* — McDonnell Boehnen Hulbert & Berghoff LLP

(57) ABSTRACT

Pharmaceutical compositions comprising a nucleic acid, a gene delivery polymer, and at least one adjunctive chemotherapeutic drug for the treatment of mammalian cancer or hyperproliferative disorders and methods of using thereof for the treatment of mammalian cancer or hyperproliferative disorders by intratumoral, intraperitoneal or systemic injection.

20 Claims, 15 Drawing Sheets

(56) References Cited

OTHER PUBLICATIONS

Hambardzumyan et al., "An update on mouse brain tumor models in cancer drug discovery", Expert Opin. Drug Discov., 2(11):1435-1451 (2007).
Meyer, "Cationic Liposomes coated with Polyethylene Glycol As Carriers for Oligonucleotides", The Journal of Biological Chemistry, 273 (25):15621-15627 (1998).
Kerbel, "Human Tumor Xenografts as Predictive Preclinical Models for Anticancer Drug Activity in Humans", Cancer Biology & Therapy 2: 4 suppl. 1, S134-139 (2003).
Prieto et al., "Gene Therapy of liver diseases", Expert Opin. Biol. Ther., 4(7):1073-1091 (2004).
Kelland, "Of mice and men': values and liabilities of the athymic nude mouse model in anticancer drug development", European Journal of Cancer, 40:827-836 (2004).
Ohlfest et al., "Nonviral Vectors for Cancer Gene Therapy: Prospects for Integrating Vectors and Combination Therapies", Current Gene Therapy, 5:629-641 (2005).
Voskoglou-Nomikos et al., "Clinical Predictive Value of the in Vitro Cell Line, Human Xenograft, and Mouse Allograft Preclinical Cancer Models", Clinical Cancer Research, 9:4227-4239 (2003).
Anwer et al., "Cationic lipid-based delivery system for systemic cancer gene therapy", Cancer Gene Therapy, 7(8):1156-1164 (2000).
Han et al., "Development of Biomaterials for Gene Therapy", Molecular Therapy, 2(4):302-317 (2000).
Roth et al., "Engineering Synthetic Vectors for Improved DNA Delivery: Insights from Intracellular Pathways:", Annu. Rev. Biomed. Eng. 6:397-426 (2004).
Goverdhana et al., "Regulatable Gene Expression systems for Gene Therapy Applications: Progress and Future Challenges", Molecular Therapy, 12(2):189-211 (2005).
Salem et al., "Novel Nonviral Deliver Approaches for Interleukin-12 Protein and Gene Systems: Curbing Toxicity and Enhancing Adjuvant Activity", Journal of Interferon and Cytokine Research, 26:593-608 (2006).
Li et al., "Gene therapy progress and prospects: non-viral gene therapy by systemic delivery", Gene Therapy, 13:1313-1319 (2006).
Janat et al., "Synergistic effects of local IL-12 gene therapy with a novel biodegradable paclitaxel delivery system", Proc. Am. Soc. Clin. Oncol. 22: abstract 933 (2003).
Jia et al., "Aerosol Gene Therapy with PEI:IL-12 Eradicates Osteosarcoma Lung Metastases", Clinical Cancer Research, 9:3462-3468 (2003).
Furgeson et al., "Tumor efficacy and 1-38 blodistribution of linear polyethylenimine-cholesterol/DNA complexes", Molecular Therapy, 9:837-845 (2004).
Fewell et al., "Synthesis and application of a non-viral gene delivery system for immunogene therapy of cancer", Journal of Controlled Release, 109:288-298 (2005).
Mahato et al., "Intratumroal Delivery of p2CMVmIL-12 Using Water-Soluble Lipopolymers", Molecular Therapy, vol. 4, 130-138 (2001).
Janat-Amsbury et al., "Combination of Lcal, Nonvirla IL12 Gene Tehrapy and Systemic Pacilataxel Treatment in a Metastatic Breast Cancer Model", Molecular Therapy, vol. 9, 829-836 (2004).
Gerson et al., "MGMT: Its Role in Cancer Aetiology and Cancer Therapeutics", Nature Reviews Cancer, vol. 4, 296-307 (2004).
Ridge et al., "A Conditioned Dendritic Cell Can be a Temporal Bridge Between a CD4+ T-helper and a T-killer Cell", Nature, vol. 393, 474-477 (1998).
Bennett et al., "Help for Cytotoxic-T-Cell Responses is Mediated by DC40 Signalling", Nature, vol. 393, 478-480 (1998).
Schoenberger et al., "T-cell Help for Cytotoxic T Lymphocytes is Mediated by CD40-CD40L Interactions", Nature, vol. 393, 480-483 (1998).
Cohen, "IL-12 Deaths: Explanation and a Puzzle", Science, vol. 270, 1-2 (1995).
Robertson et al., "Interleukin 12: Basic Biology and potential Applications in Cancer Treatment", The Oncologist, vol. 1, 88-97 (1996).
Anwer et al., "Recent Progress in Polymeric Gene Delivery Systems," Critical Reviews (TM) in Therapeutic Drug Carrier Systems, vol. 20(4):249-293 (2003).
Maruyama-Tabata et al, "Effecitve Suicide Gene Therapy in Vivo by EBV-based Plasmid Vector Coupled with Polyamidoamine Dendrimer", Gene Therapy, vol. 7, 53-60 (2000).
Maheshari et al., "Biodegradable Polymer-based Interleukin-12 Gene Delivery: Role of Induced Cytokines, Tumor Infiltrating Cells and Nitric Oxide in Anti-Tumor Activity", Gene Ther., vol. 9, 1075-1084 (2002).
Nakanishi et al., "Nonviral Genetic Transfer of Fas Ligand Induced Significant Growth, Suppression and Apoptotic Tumor Cell Death in Prostate Cancer in Vivo", Gene Ther, vol. 10, 434-442 (2003).
Coleman et al., "Nonviral Interferon a Gene Therapy Inhibits Growth of Established Tumors by Eliciting a Systemic Immune Response", Hum. Gene Ther., vol. 9, 2223-2230 (1998).
Zagozdzon et al., "Effective chemo-Immunotherapy of L1210 Leukemia In Vivo Using Interleukin-12 Combined with Doxorubicin but not with Cyclophosphamide Paclitaxel or Cisplatin", Int. J. Cancer, vol. 77, 720-727 (1998).
Yockman et al., "Tumor Regression by Repeated Intratumoral Delivery of Water Soluble Lipopolymers/p2CMVmIL-12 Complexes", J. Control Release, vol. 87, 177-186 (2003).
Tsung et al., "Immuno Response Against Large Tumoors Eradicated by Treatment with Cyclophosphamide and IL-12", J. Immunol., vol. 160, 1369-1377 (1998).
Tare et al., "Administration of Recombinant Interleukin-12 to Mice Suppresses Hemotopoiesis in the Bone Marrow but Enhances Hematopoiesis in the Spleen", J. Interferon Cytokine Res., vol. 15, 377-383 (1995).
Sarmiento et al., "Biologic Effects of Recombinant Human Interleukin-12 in Squirrel Monkeys", Lab Invest., vol. 71, 862-873 (1994).
Daqing et al., "Combination Nonviral Cytokine Gene Therapy for Head and Neck Cancer", Laryngoscope, vol. 111, 815-820 (2001).
Janat-Amsbury et al., "Combination of Local, Nonvirl IL12 Gene Therapy and Systemic Paclitaxel Treatment in a Metastatic Breast Cancer Model", Molecular Therapy, vol. 9, No. 6, 829-836 (2004).
Oshikawa et al., Journal of Clinical and Experiemental Medicine (Syuukann Igaku no Ayumi), vol. 188, No. 7, 768-769 (1999).
Urushizaki, Antibiotics & Chemotherapy (Kagaku Ryouhou no Ryouiki), vol. 10, No. 6, 1031-1037 (1994).
Japanese Domestic Announcement (kohyo) No. 2004-522809, dated Jul. 29, 2004.
Ogris et al., "Tumor-targeted gene therapy: strategies for the preparation of ligand-polyethylene glycol-polyethyleniminie/DNA complexes", Journal of Controlled Release, 91:173-181 (2003).

COMBINATION OF IMMUNO GENE THERAPY AND CHEMOTHERAPY FOR TREATMENT OF CANCER AND HYPERPROLIFERATIVE DISEASES

PRIORITY CLAIM

This application is a continuation of U.S. Ser. No. 11/261,931, filed on Oct. 28, 2005 (now allowed), which claims the benefit of U.S. Ser. No. 60/635,042, filed on Dec. 9, 2004, both of which are incorporated herein by reference in their entirety.

FIELD OF THE INVENTION

This invention relates to pharmaceutical compositions comprising a nucleic acid, a gene delivery polymer, and at least one adjunctive chemotherapeutic drug for the treatment of mammalian cancer or hyperproliferative disorders. This invention also relates to methods of treating mammalian cancer or hyperproliferative disorders, said method comprising contacting cancer cells or any other hyperproliferative cells with said compositions by intratumoral, intraperitoneal or systemic injection.

BACKGROUND OF THE INVENTION

Cancer is the most common cause of death in many parts of the world and over 2.5 million cases of cancer are diagnosed globally every year. Recent advances in our understanding of the molecular biology of cancer have shown that cancer is a genetic disease resulting in the abnormal proliferation of the affected cell. Therefore, cancer therapists are now focusing on therapeutic strategies that involve macromolecules carrying genetic information, rather than a therapeutic protein itself, allowing for the exogenously delivered genes to be expressed in the tumor environment. Gene therapy is believed to offer therapeutic benefits to cancer patients in a number of ways that are not possible with conventional approaches. Traditional small molecule drugs usually function by non-specific interaction with the cellular targets, produce undesirable side effects and do not treat the root cause of the disease. Protein drugs which have been introduced over the last several years have their own limitations due to their rapid degradation and high doses that are required which often leads to undesirable side effects. Gene therapy uses the body's own cellular machinery to produce sustained therapeutic levels of proteins in specific tissues and cells after a single injection, thus providing a safe and effective method of treatment with better patient compliance.

The most commonly applied cancer gene therapy strategies include immunotherapy, cell ablation and anti-angiogensis accomplished by 1) local, 2) loco-regional, or 3) systemic injection. Cancer immunotherapy is a potent approach to combat cancer by stimulating the immune system against the cancer cells. Immunocytokines play an important role in the development of the host immune response by activation, maturation and differentiation of the immune cells. Several cytokines have been tested against a variety of cancers in human and in animal models of cancers. See *Hum Gene Ther.*, 1998, vol. 9, 2223; *Gene Ther.* 1999, vol. 6, 833; *Cancer Gene Ther.* 2000, vol. 7, 1156; *J. Control Rel.* 2003, vol. 87, 177; and *Cancer Res.*, 2002, vol. 62, 4023. Interleukin 12 (IL-12) is an immunostimulatory cytokine that shows great promise in the treatment of human cancer. See *The Oncologist,* 1996, vol. 1, 88. IL-12 is a 70-kD heterodimer consisting of two covalently linked chains, p35 and p40. The biological effects of IL-12 include the induction of IFN-γ production both by resting and activated CD4+ T cells, CD8+ T cells, and natural killer (NK) cells. IL-12 also enhances the proliferation of activated T and NK cells, increases the lytic activity of NK/lymphokine-activated killer cells, and facilitates specific cytotoxic T lymphocyte (CTL) responses.

In animal models, recombinant IL-12 has been demonstrated to induce profound T-cell mediated antitumor effects causing regression of established tumors, followed by systemic immune memory. See *The Oncologist,* 1996, vol. 1, 88. However, systemic administration of recombinant IL-12 has resulted in dose limiting toxicity in several experimental trials and in an initial human trial. See *Lab Invest.,* 1994, vol. 71, 862; *Science,* 1995, vol. 270, 908; *J. Interferon Cytokine Res.,* 1995, vol. 14, 335. Dose limiting toxicity was also observed with intraperitoneal administration of recombinant IL-12 in a recent human clinical trial. *Clin. Cancer Res.,* 2002, vol. 8, 3686. A gene delivery approach that can provide therapeutic levels of IL-12 locally at the tumor site would have the advantage of generating an anticancer response without causing systemic toxicity.

Both viral and non-viral gene delivery systems have been used for IL-12 gene delivery in animal models of cancer. The viral approach has serious practical limitations due to toxicity concerns mainly because of an increased incidence of cancer and a strong immune reaction to viral antigens by the host system. There is considerable interest in the development of non-viral gene delivery systems due to their lesser toxicity. Using polyvinylpyrrolidone (PVP), a non-viral gene delivery system, for the delivery of IL-12 to treat renal carcinoma (Renca) and colon cell carcinoma (CT26) has been demonstrated. See *Gene Ther.,* 1999, vol. 6, 833. When tumors were subjected to this gene therapy, they displayed all the characteristics of IL-12 protein therapy, e.g., an increased infiltration of NK cells, CD4 and CD8 T cells, coupled with an increased expression of major histocompatibility complex (MHC) class I molecules. IL-12 gene delivery was well tolerated and highly effective against both Renca and CT26 tumor bearing animals. Tumor rejecting mice were also protected from a subsequent rechallenge, suggesting the presence of a long lasting systemic immunity. A functionalized and less toxic water soluble lipopolymer (WSLP) has been tested for delivery of the IL-12 gene to CT26 colon carcinoma tumors. See Mahato et al, *Mol. Ther.,* 2001, vol. 4, 130. IL-12 plasmid (pIL-12) and WSLP (pIL-12/WSLP) treatment gave higher levels of intratumoral gene expression than naked DNA.

Furthermore, secondary effects of the cytokine IL-12 production, namely IFN-γ and nitric oxide (NO) levels were also higher in WSLP treated tumors when compared with naked DNA. A single injection of pIL-12/WSLP complexes produced suboptimal effects on tumor growth and animal survival, while repeated delivery yielded better efficacy which indicates insufficient delivery by the system. *J. Control Release* 2003, vol. 87, 177. Similarly, intratumoral injection of IL-12 plasmid in another polymeric carrier, PAGA, produced only partial inhibition of CT26 tumors. See *Gene Ther.,* 2002, vol. 9, 1075. These results warrant the need for more efficient delivery systems. Despite their insufficiencies in earlier preclinical trials, the excellent molecular flexibility of polymeric gene carriers allows for complex modification and novel functionalization imperative for the development of more efficient gene delivery systems.

It is widely recognized that employing a single treatment strategy against cancer is generally ineffective due to the multi-factorial nature of this disease. The combination of more than one drug to maximize the anticancer response is being increasingly utilized. See *Gene Ther.*, 2000, vol. 11, 1852. It has been demonstrated that there is a synergistic relationship between IL-12 gene therapy and IFN-α gene therapy. Co-treatment of Renca tumors with these two genes led to 100% tumor rejection which was higher than that achieved by treatments with either IL-12 (58%) or IFN-α (25%) alone. Similarly, CT26 tumors showed a 50% rejection rate with combination gene therapy which was higher than the 17% and 0% rejection rate achieved from single treatments of IL-12 and IFN-α, respectively. Tumors treated by combination therapy showed increased tumor-infiltration of NK and CD8 T cells when compared to tumors treated by single gene therapy. Gene transfer of methylguanine-DNA-methyltransferase (MGMT) into stem cells alongside with chemotherapy protected normal cells from chemotherapy and reduced chemotherapy systemic toxicity. *Nature Reviews Cancer* 2004, vol. 4, 296.

Furthermore, combination gene therapy increased the number of CD40 molecules on antigen presenting cells (APCs) in the tumors to levels higher than was achieved with single treatments. Increased upregulation of CD40 on APCs is associated with higher activation status for antigen presentation. See *Nature*, 1998, vol. 393, 480; *Nature*, 1998, vol. 393, 474; and *Nature*, 1998, vol. 393, 478. A similar increase was observed in the levels of mRNA for the chemokines IP-10 and TCA-3. Combination gene therapy therefore synergistically enhanced the anti-tumor immunity and this effect was found to be long lasting in tumor rechallenge studies. Similar combination gene therapy studies have been reported by other groups. See *Laryngoscope* 2001, vol. 111, 815. Established tumors were treated with pIFN-α/PVP, pIL-2/lipid, or pIL-12/PVP alone or a combination thereof. The pIFN-α/PVP combination compared with the other two therapies significantly increased the antitumor effects when compared with single treatments. In another study utilizing the same tumor model, it has been demonstrated that combined treatment with pIL-12/PVP and pIL-2/lipid gave significantly higher anti-tumor effects when compared with single treatments. See *Arch. Otolaryngol Head Neck Surg*, 2001, vol. 127, 1319.

In another study, intratumoral injection of polyplexes of linear polyethylenimine (PEI) with an anti-oncogene and somatostatin receptor subtype 2 (sst2), produced a significant inhibition of growth of pancreatic tumors and metastases to the liver. *Curr Opin Biotechnol*, 2002, vol. 13, 128. The PEI-mediated delivery of sst2 in tumors led to increased apoptosis and activation of the caspase-3 and poly(ADP-ribose) pathways. Sustained delivery of DNA/PEI polyplexes into solid tumors produced higher expression than achieved by bolus delivery. *Gene Ther.*, 1999, vol. 10, 1659. Dendrimers were used for inhibition of pancreatic carcinoma and hepatocellular carcinoma by intratumoral gene transfer of Fas-L and HSV-1 thymidine kinase, respectively. See *Gene Ther.*, 2003, vol. 10, 434; and *Gene Ther.*, 2000, vol. 7, 53.

Chemo-immunotherapy using cytotoxic drugs and cytokines offers a new approach for improving the treatment of neoplastic diseases. The therapeutic efficacy of combinations of IL-12 proteins with cyclophosphamide, paclitaxel, cisplatin or doxorubicin has been investigated in the murine L1210 leukemia model. See *Int. J. Cancer*, 1998, vol. 77, 720. Treatment of L1210 leukemia with IL-12 or one of the above chemotherapeutic agents given alone resulted in moderate antileukemic effects. Combination of IL-12 with cyclophosphamide or paclitaxel produced no augmentation of antileukemic effects in comparison with these agents given alone. However, combination of IL-12 with doxorubicin augmented the antileukemic effect, while combination with cisplatin had a moderate enhancing effect.

However, in murine melanoma MmB16 model the IL-12+paclitaxel combination was more effective than the individual therapies. *Cancer Lett.*, 1999, vol. 147, 67. The antitumor efficacy of IL-12 protein in combination with adriamycin, cyclophosphamide, or 5-FU in MB-49 bladder carcinoma and B16 melanoma has also been examined. See, *Clin. Cancer Res.*, 1997, vol. 3, 1661. In combination with chemotherapy, IL-12 administration increased antitumor activity without causing additional toxicity. In mouse sarcoma MCA207 that is refractory to treatment by either IL-12 or cyclophosphamide, combination of recombinant IL-12 and cyclophosphamide gave a better antitumor response than the individual treatments. *J Immunol.*, 1998, vol. 160, 1369. In mouse mammary tumors, combination therapy comprising intravenous paclitaxil chemotherapy and intratumoral IL-12 gene therapy (IL-12/WSLP) was more efficacious than the individual therapies. See, *Molecular Therapy*, 2004, vol. 9, 829. The benefit of this combination therapy was dependent on the delivery vehicle used for paclitaxel. The synergistic interaction between paclitaxel and IL-12 gene therapy was observed when paclitaxel was formulated in a polymeric formulation. In comparison, combination with Cremophor EL (Taxol®), a widely used paclitaxel formulation for cancer therapy, was not synergistic, suggesting that the observed benefits were formulation specific.

To achieve a desirable outcome from a combination approach involving gene therapeutics, the selection of an appropriate gene delivery system is important. The gene delivery system used in the aforementioned combination experiments (*Molecular Therapy*, 2004, vol. 9, 829) is a water soluble lipopolymer, PEI-Cholesterol (WSLP). In the present invention, we describe the use of a novel class of polymeric carriers (PEG-PEI-Cholesterol) structurally distinct from WSLP in that it contains a hydrophilic polymer designed to improve pharmacokinetics, safety and potency of the gene delivery system and membrane interacting ligands (e.g., cholesterol) that are oriented in numerous geometrical configurations to promote transfection activity of anticancer genes either alone or in combination with a chemotherapeutic agent. The transfection activity advantage of PPC compared to WSLP in tumor tissue is illustrated in FIG. 1 and FIG. 2.

The combination of either two chemotherapeutic agents or a chemotherapeutic agent and a cytokine has been examined clinically. Although these combinations have produced greater tumor regression, the long-range survival benefits are marginal and cytotoxicity has been a problem. This is due to the inherent systemic toxicity associated with chemotherapy and recombinant protein therapy. New and more effective combinational approaches must be designed to improve future cancer therapy. In this present invention, we describe a novel combinational approach for treatment of cancer comprising a nucleic acid based therapeutic delivered with a polymeric carrier and at least one chemotherapeutic agent.

BRIEF SUMMARY OF THE INVENTION

This present invention provides pharmaceutical compositions comprising a nucleic acid, a gene delivery polymer, and at least one pharmaceutical agent for the treatment of cancer. In addition, the present invention also provides a method for inhibiting the growth and metastasis of tumor cells and improving survival in mammals by the in vivo administration of pharmaceutical compositions comprising a nucleic acid, a gene delivery polymer, and at least one pharmaceutical agent.

The nucleic acid is a member selected from the group consisting of plasmid DNA, siRNA, sense RNA, antisense RNA, and ribozymes. The plasmid DNA is a gene expression system containing a DNA sequence which encodes for an anticancer or anti-proliferative protein selected from the group consisting of interleukin-2, interleukin-4, interleukin-7, interleukin-12, interleukin-15, interferon-α, interferon-β, interferon-γ, colony stimulating factor, granulocyte-macrophage stimulating factor, anti-angiogenic agents, tumor suppressor genes, thymidine kinase, eNOS, iNOS, p53, p16, TNF-α, Fas-ligand, mutated oncogenes, tumor antigens, viral antigens or bacterial antigens. The plasmid DNA may also encode for an shRNA molecule designed to inhibit protein(s) involved in the growth or maintenance of tumor cells or other hyperproliferative cells. A plasmid DNA may simultaneously encode for a therapeutic protein and one or more shRNA. Furthermore, the nucleic acid of the said composition may also be a mixture of plasmid DNA and synthetic RNA including sense RNA, antisense RNA or ribozymes.

The gene delivery polymer is a cationic polymer or a non-condensing polymer. The cationic polymer is selected from the group comprising polylysine, polyethylenimine, functionalized derivatives of polyethylenimine (PEI), polypropylenimine, aminoglycoside-polyamine, dideoxy-diamino-b-cyclodextrin, spermine and spermidine. One example of a cationic gene delivery polymer suitable for the present invention is a PEI derivative comprising a PEI backbone, a lipid, and a hydrophilic polymer spacer wherein the lipid is directly bound to the polyethylenimine backbone or covalently bound to the polyethylene glycol spacer, which in turn is bound, via a bio compatible bond, to the PEI. The cationic gene delivery polymer of the present invention may further comprise a targeting moiety including antibodies or antibody fragments, cell receptors, growth factor receptors, cytokine receptors, folate, transferrin, epidermal growth factor (EGF), insulin, asialoorosomucoid, mannose-6-phosphate (monocytes), mannose (macrophage, some B cells), Lewis$^x$ and sialyl Lewis$^x$ (endothelial cells), N-acetyllactosamine (T cells), galactose (colon carcinoma cells), and thrombomodulin (mouse lung endothelial cells), fusogenic agents such as polymixin B and hemaglutinin HA2, lysosomotrophic agents, nucleus localization signals (NLS) such as T-antigen, and the like. Another gene delivery polymer is a non-condensing polymer selected from the group comprising polyvinylpyrrolidone, polyvinylalcohol, poly(lactide-co-glycolide) (PLGA) and triblock copolymers of PLGA and PEG. The gene delivery polymer may also be a non-condensing polymer. Examples of such non-condensing polymers include polyvinyl pyrollidone, polyvinyl alcohol, poloxamers, polyglutamate, gelatin, polyphosphoesters, silk-elastin-like hydrogels, agarose hydrogels, lipid microtubules, poly(lactide-co-glycolide) and polyethyleneglycol-linked poly(lactide-co-glycolide).

In one embodiment of the foregoing composition the pharmaceutical agent is a chemotherapeutic drug selected from the group consisting of taxanes, platinums, adriamycins, cylcophosphamide, topotecan, carmustine (BCNU) or a combination thereof. Paclitaxel, carboplatin, topotecan, gemcitabine and any combination thereof are particularly preferred.

In another embodiment of the foregoing compositions the pharmaceutical agent is an anti-cancer antibody selected from the group consisting of CD20 antibody, HER2/neu antibody, anti-VEGF antibody, epidermal growth factor receptor antibody and radioisotopic conjugates thereof.

This present invention also provides a method for treatment of mammalian cancer by intratumoral, intraperitoneal, intratracheal, intracranial or systemic administration of pharmaceutical compositions comprising a nucleic acid, a nucleic acid delivery polymer, and at least one adjunctive chemotherapeutic drug. The mammalian cancer is selected from a group consisting of primary or metastasized tumors of ovary, breast, brain, head and neck, liver, lung, prostate, kidney, colon, pancreas, thyroid, urinary bladder, abdominal cavity, thoracic cavity and skin. The nucleic acid and gene delivery polymer is administered by intratumoral, intraperitoneal, intratracheal or oral or systemic administration before or after the administration of the pharmaceutical agents. For example, in some instances it is preferred to administer the nucleic acid (e.g., pIL-12 DNA/polymer) prior to the pharmaceutical agent (e.g., chemotherapy), as this would potentially enhance tumor sensitivity to the pharmaceutical agent and boost the anti-cancer response. In another instance, it is preferred to give the pharmaceutical agent (e.g., chemotherapy) prior to gene delivery (e.g., pIL-12/PPC) to allow the pharmaceutical agent to cause tumor destruction and release of tumor antigens later to be used by the therapeutic gene (e.g., pIL-12/polymer) for eliciting highly specific and robust therapeutic response (e.g., immune response) against the target cancer.

The treatment of tumors with the said pharmaceutical composition (nucleic acid plus gene delivery polymer and one or more chemotherapeutic agents) results in tumor shrinkage and extension of life span. The combination of gene therapy (nucleic acid and gene delivery polymers) with chemotherapy (chemotherapeutic agents) according to the method of the present invention produce additive and/or synergistic efficacy. The efficacy of the method of this invention is defined as but not limited to shrinkage in tumor size or reduction in tumor density, an increase in lymphocyte count or increase in neutrophil count or improvement in survival, or all of the above. In addition, the combination of gene therapy (nucleic acid and gene delivery polymers) with chemotherapy (chemotherapeutic agents) according to the method of the present invention lowers the toxicity of the chemotherapeutic agent and reverses tumor resistance to chemotherapy. The toxicity herein is defined as any treatment related adverse effects on clinical observation including but not limited to abnormal hematology or serum chemistry or organ toxicity. Furthermore, the combination of gene therapy (nucleic acid and gene delivery polymers) with a suboptimal dose of chemotherapy (chemotherapeutic agents) according to the method of the present invention enhances the anticancer effect to a level equal to or higher than that of achieved with the optimal dose of the chemotherapeutic agent but with lesser toxicity.

In the said combination therapy, the nucleic acid is a member selected from the group consisting of plasmid DNA, siRNA, sense RNA, antisense RNA, and ribozymes. The nucleic acid can be a plasmid-based gene expression system containing a DNA sequence which encodes for an anticancer or anti-proliferative protein selected from the group consisting of interleukin-2, interleukin-4, interleukin-7, interleukin-12, interleukin-15, interferon-α, interferon-β, interferon-γ, colony stimulating factor, granulocyte-macrophage stimulating factor, anti-angiogenic agents, tumor suppressor genes, thymidine kinase, eNOS, iNOS, p53, p16, TNF-α, Fas-ligand, mutated oncogenes, tumor antigens, viral antigens or bacterial antigens. The plasmid DNA may also encode for an shRNA molecule designed to inhibit protein(s) involved in the growth or maintenance of tumor cells or other hyperproliferative cells. A plasmid DNA may simultaneously encode for a therapeutic protein and one or more shRNA molecules. Furthermore, the nucleic acid of the said composition may also be a mixture of plasmid DNA and synthetic RNA. The gene delivery polymer is a cationic polymer or a non-condensing polymer. The cationic polymer is selected from the group comprising polylysine, polyethylenimine, functionalized derivatives of polyethylenimine, polypropylenimine, aminoglycoside-polyamine, dideoxy-diamino-b-cyclodextrin, spermine and spermidine. One example of a cationic gene delivery polymer suitable for the present invention is a polyethylenimine derivative comprising a polyethylenimine (PEI) backbone, a lipid, and a polyethylene glycol spacer wherein the lipid is directly bound to the polyethylenimine backbone or covalently bound to the polyethylene glycol spacer, which in turn is bound, via a biocompatible bond, to the PEI. The cationic gene delivery polymer of the present invention may further comprise a targeting moiety including antibodies or antibody fragments, cell receptors, growth factor receptors, cytokine receptors, folate, transferrin, epidermal growth factor (EGF), insulin, asialoorosomucoid, mannose-6-phosphate (monocytes), mannose (macrophage, some B cells), Lewis$^x$ and sialyl Lewis$^x$ (endothelial cells), N-acetyllactosamine (T cells), galactose (colon carcinoma cells), and thrombomodulin (mouse lung endothelial cells), fusogenic agents such as polymixin B and hemaglutinin HA2, lysosomotrophic agents, nucleus localization signals (NLS) such as T-antigen, and the like. The gene delivery polymer is a non-condensing polymer selected from the group comprising polyvinylpyrrolidone, polyvinylalcohol, poly(lactide-co-glycolide) (PLGA) and triblock copolymers of PLGA and PEG. The chemotherapeutic drug is a member selected from the group consisting of texanes, platinums, adriamycins, cylcophosphamide, topotecan, carmustine (BCNU) or a combination thereof. Paclitaxel, carboplatin, topotecan, gemcitabine and any combination thereof are particularly preferred.

In another embodiment of the foregoing method the pharmaceutical agent is an anti-cancer antibody selected from the group consisting of CD20 antibody, HER2/neu antibody, anti-VEGF antibody, epidermal growth factor receptor antibody and radioisotopic conjugates thereof.

This present invention also provides a method for treatment of mammalian cancer or hyperproliferative disorders by intratumoral, intraperitoneal, intratracheal, intracranial or systemic administration of pharmaceutical compositions comprising a plasmid-based gene expression system and a gene delivery polymer, without a chemotherapeutic drug. The mammalian cancer is selected from a group consisting of primary or metastasized tumors of ovary, breast, brain, head and neck, thyroid, liver, lung, pancreas, intestine, spleen, prostate, kidney, urinary bladder, colon, and melanoma. Preferably, the nucleic acid is a plasmid-based gene expression system containing a DNA sequence which encodes an anti-cancer or anti-proliferative protein selected from the group consisting of interleukin-2, interleukin-4, interleukin-7, interleukin-12, interleukin-15, interferon-$\alpha$, interferon-$\beta$, interferon-$\gamma$, colony stimulating factor, granulocyte-macrophage stimulating factor, anti-angiogenic agents, tumor suppressor genes, thymidine kinase, eNOS, iNOS, p53, p16, TNF-$\alpha$, Fas-ligand, mutated oncogenes, tumor antigens, viral antigens or bacterial antigens. The plasmid DNA may also encode for an shRNA molecule designed to inhibit protein(s) involved in the growth or maintenance of tumor cells or other hyperproliferative cells. A plasmid DNA may simultaneously encode for a therapeutic protein and one or more shRNA molecules. Furthermore, the nucleic acid of the said composition may also be a mixture of plasmid DNA and synthetic RNA.

The gene delivery polymer of the said composition is a cationic polymer or a non-condensing polymer. The cationic polymer is selected from the group comprising polyethylenimine, functionalized derivatives of polyethylenimine, polypropylenimine, aminoglycoside-polyamine, dideoxy-diamino-b-cyclodextrin, spermine and spermidine. One example of a cationic polymer suitable for presentation is a polyethylenimine derivative comprising polyethylenimine (PEI), a lipid, and a hydrophilic polymer spacer wherein the lipid is directly bound to the polyethylenimine backbone or covalently bound to the hydrophilic polymer spacer, which in turn is bound via a biocompatible bond to the PEI. The cationic polymer of the present invention may further comprise a targeting moiety including antibodies or antibody fragments, cell receptors, growth factor receptors, cytokine receptors, folate, transferrin, epidermal growth factor (EGF), insulin, asialoorosomucoid, mannose-6-phosphate (monocytes), mannose (macrophage, some B cells), Lewis$^x$ and sialyl Lewis$^x$ (endothelial cells), N-acetyllactosamine (T cells), galactose (colon carcinoma cells), and thrombomodulin (mouse lung endothelial cells), fusogenic agents such as polymixin B and hemaglutinin HA2, lysosomotrophic agents, nucleus localization signals (NLS) such as T-antigen, and the like. Another gene delivery polymer is a non-condensing polymer selected from the group comprising polyvinylpyrrolidone, polyvinylalcohol, poly(lactide-co-glycolide) (PLGA) and triblock copolymers of PLGA and PEG. The treatment of tumors with the pharmaceutical composition (nucleic acid plus gene delivery polymer and one or more chemotherapeutic agent) results in tumor shrinkage and extension of the life span.

DETAILED DESCRIPTION

Figure 1:
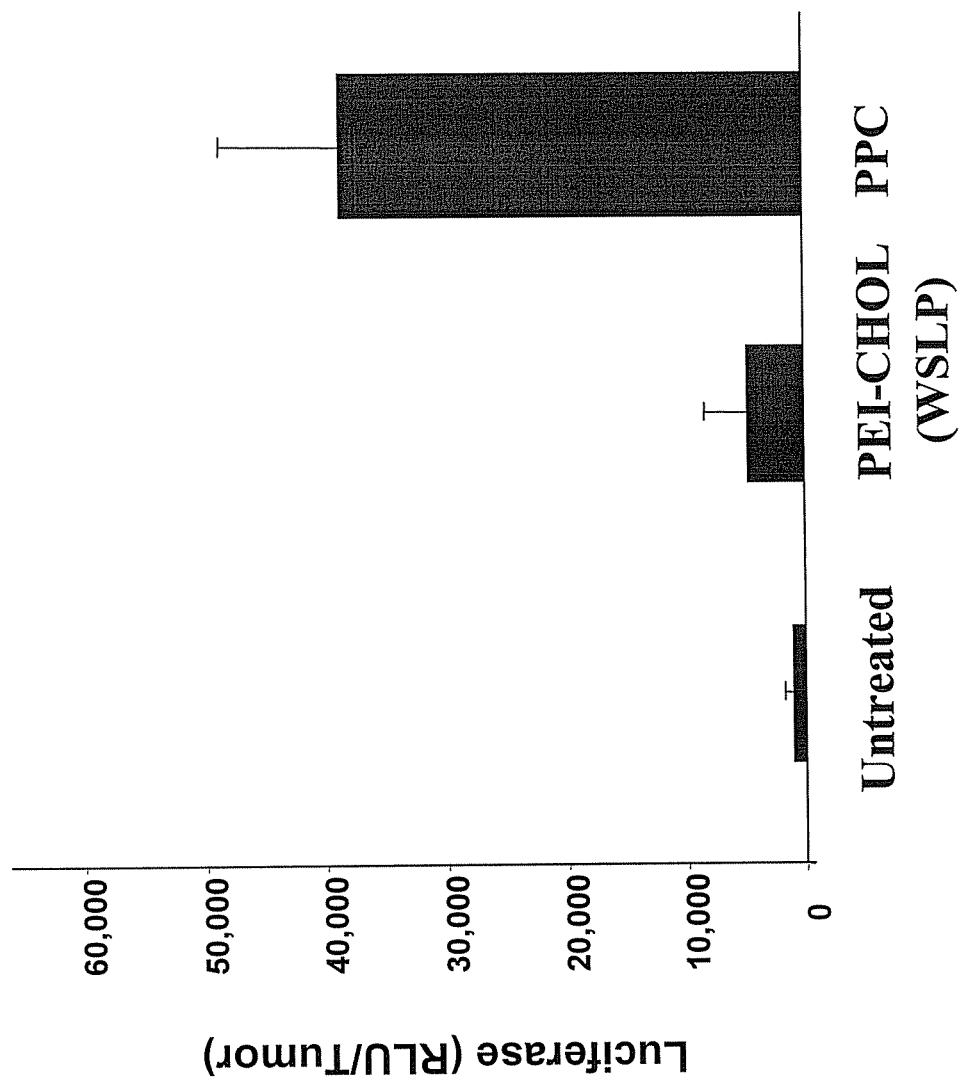
FIG. 1 illustrates the difference in the efficiency of gene transfer between the gene delivery polymers PEG-PEI-Cholesterol (PPC) and a water soluble lipopolymer, PEI-Chol (WSLP). The test polymers were complexed with a luciferase plasmid and administered intratumorally into 4T1 breast tumors. Luciferase expression was quantified in tumor tissues 24 hours thereafter.

Before the present composition and method for delivery of a bioactive agent are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a polymer containing "a disulfide link" includes reference to two or more of such disulfide links, reference to "a ligand" includes reference to one or more of such ligands, and reference to "a drug" includes reference to two or more of such drugs.

In describing and claiming the present invention, the following terminology will be used in accordance with the definitions set out below.

"Transfecting" or "transfection" shall mean transport of nucleic acids from the environment external to a cell to the internal cellular environment, with particular reference to the cytoplasm and/or cell nucleus. Without being bound by any particular theory, it is to be understood that nucleic acids may be delivered to cells either after being encapsulated within or adhering to one or more cationic polymer/nucleic acid complexes or being entrained therewith. Particular transfecting instances deliver a nucleic acid to a cell nucleus. Nucleic acids include DNA and RNA as well as synthetic congeners thereof. Such nucleic acids include missense, antisense, nonsense, as well as protein producing nucleotides, on and off and rate regulatory nucleotides that control protein, peptide, and nucleic acid production. In particular, but not limited to, they can be genomic DNA, cDNA, mRNA, tRNA, rRNA, hybrid sequences or synthetic or semi-synthetic sequences, and of natural or artificial origin. In addition, the nucleic acid can be variable in size, ranging from oligonucleotides to chromosomes. These nucleic acids may be of human, animal, vegetable, bacterial, viral, or synthetic origin. They may be obtained by any technique known to a person skilled in the art.

As used herein, the term "pharmaceutical agent" or "drug" or any other similar term means any chemical or biological material or compound suitable for administration by the methods previously known in the art and/or by the methods taught in the present invention, which induce a desired biological or pharmacological effect, which may include but are not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating a disease from the organism. The effect may be local, such as providing for a local anesthetic effect, or it may be systemic.

This invention is not drawn to novel drugs or to new classes of bioactive agents per se. Rather it is drawn to biocompatible cationic copolymer compositions and methods of using such compositions for the delivery of genes or other bioactive agents that exist in the state of the art or that may later be established as active agents and that are suitable for delivery by the present invention. Such substances include broad classes of compounds normally delivered into the body. In general, this includes but is not limited to: nucleic acids, such as DNA, RNA, and oligonucleotides, anti-infective such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium, calcium channel blockers, beta-blockers, alpha-blockers, and antiarrhythmics; antihypertensives; diuretics and antidiuretics; vasodilators including general, coronary, peripheral and cerebral; central nervous system stimulants; vasoconstrictors; cough and cold preparations, including decongestants; hormones such as estradiol and other steroids including corticosteroids; hypnotics; immunosuppressives; muscle relaxants; parasympatholytics; psychostimulants; sedatives; and tranquilizers. By the method of the present invention, drugs in all forms, e.g. ionized, nonionized, free base, acid addition salt, and the like may be delivered, as can drugs of either high or low molecular weight. The only limitation to the genus or species of bioactive agent to be delivered is that of functionality which can be readily determined by routine experimentation.

As used herein, the term "biocompatible" or "biodegradation" is defined as the conversion of materials into less complex intermediates or end products by solubilization hydrolysis, or by the action of biologically formed entities which can be enzymes and other products of the organism.

As used herein, "effective amount" means the amount of a nucleic acid or a bioactive agent that is sufficient to provide the desired local or systemic effect and performance at a reasonable risk/benefit ratio as would attend any medical treatment.

As used herein, "peptide" means peptides of any length and includes proteins. The terms "polypeptide" and "oligopeptide" are used herein without any particular intended size limitation, unless a particular size is otherwise stated. Typical of peptides that can be utilized are those selected from the group consisting of oxytocin, vasopressin, adrenocorticotrophic hormone, epidermal growth factor, prolactin, luliberin or luteinising hormone releasing hormone, growth hormone, growth hormone releasing factor, insulin, somatostatin, glucagon, interferon, gastrin, tetragastrin, pentagastrin, urogastroine, secretin, calcitonin, enkephalins, endorphins, angiotensins, renin, bradykinin, bacitracins, polymixins, colistins, tyrocidin, gramicidines, and synthetic analogues, modifications and pharmacologically active fragments thereof, monoclonal antibodies and soluble vaccines. The only limitation to the peptide or protein drug which may be utilized is one of functionality.

As used herein, a "derivative" of a carbohydrate includes, for example, an acid form of a sugar, e.g. glucuronic acid; an amine of a sugar, e.g. galactosamine; a phosphate of a sugar, e.g. mannose-6-phosphate and the like.

As used herein, "administering" and similar terms mean delivering the composition to the individual being treated such that the composition is capable of being circulated systemically where the composition binds to a target cell and is taken up by endocytosis. Thus, the composition is preferably administered systemically to the individual, typically by subcutaneous, intramuscular, transdermal, intravenous, or intraperitoneal routes. Injectables for such use can be prepared in conventional forms, either as a liquid solution or suspension, or in a solid form that is suitable for preparation as a solution or suspension in a liquid prior to injection, or as an emulsion. Suitable excipients that can be used for administration include, for example, water, saline, dextrose, glycerol, ethanol, and the like; and if desired, minor amounts of auxiliary substances such as wetting or emulsifying agents, buffers, and the like.

As used herein, "efficacy" and similar terms means disappearance of tumor or shrinkage of tumor in size or reduction in tumor density or increase in lymphocyte count or increase in neutrophil count or improvement in survival, or all of the above.

As used herein, "toxicity" is defined as any treatment related adverse effects on clinical observation including but not limited to abnormal hematology or serum chemistry results or organ toxicity.

New cancer treatment strategies are focused on delivering macromolecules carrying genetic information, rather than a therapeutic protein itself, allowing for the exogenously delivered genes to be expressed in the tumor environment. Methods that utilize non-viral gene delivery systems are considered safer compared to viral delivery systems, but the practical application of current polymeric systems has not been satisfactory due to poor efficiency. A strategy has recently been disclosed whereby the gene transfection efficiency of a low molecular weight PEI was enhanced by covalent attachment of cholesterol forming a water soluble lipopolymer (WSLP). See, *Mol. Ther.*, 2001, 4, 130. IL-12 gene transfer to solid tumors with WSLP was significantly better than by the unmodified PEI and led to more significant tumor inhibition.

Figure 2:
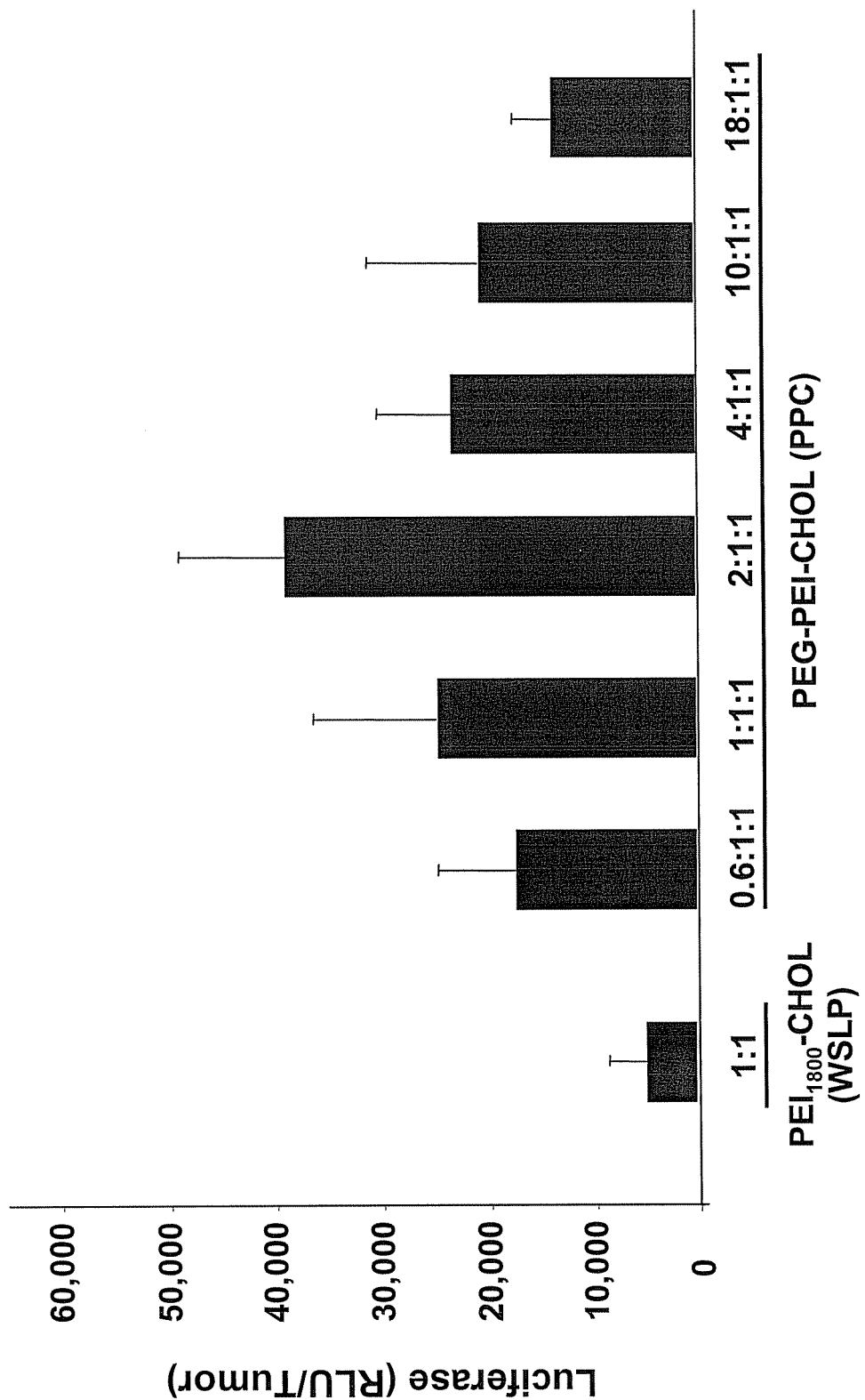
FIG. 2 illustrates the effect of increasing the PEG:PEI ratio in PEG-PEI-Chol on the efficiency of gene transfer into solid 4T1 tumors by intratumoral administration of plasmid/PPC complexes. The PPC polymer, synthesized at different PEG:PEI ratios, was complexed with a luciferase plasmid and administered intratumorally into 4T1 breast tumors. Luciferase expression was quantified in tumor tissues 24 hours thereafter.

The present invention provides a novel polymeric system, PEG-PEI-Cholesterol (PPC), which differs from WSLP (PEI-Cholesterol) in that it contains PEG moieties and yields significantly higher transfection efficiency in tumors (FIG. 1). The addition of PEG is designed to enhance the stability of the nucleic acid/polymer complexes in the biological milieu to circumvent for this deficiency in the prior art (WSLP). Furthermore, the addition of PEG chains allows for the incorporation of ligands on to the PPC chain to improve the tissue selectivity of delivery. For example, the cholesterol moiety which is directly linked to the PEI back bone in the prior art (WSLP) may be extended farther from the PEI backbone to create a more flexible geometry for cell receptor interaction. Controlling the number of PEG molecules per unit of the PEI backbone is important to achieve optimal enhancement in transfection activity. As illustrated in FIG. 2, the magnitude of tumor gene transfer is dependent on the ratio between the different PPC components, the PEG, PEI and cholesterol. A preferred range of composition was a PEG:PEI molar ratio of 2-4 at a fixed cholesterol content. The optimal ratio between PEI and cholesterol was 1:0.5 to 1:1. The ability of PPC to promote gene transfer into tumors was examined with a therapeutic gene. Expression plasmid containing mouse IL-12 genes (pmIL-12) were complexed with PPC at a nitrogen (N) to phosphate (P) ratio (N:P ratio) of 11:1 and administered intratumorally into mice with solid 4T1 tumors or intraperitoneally in mice with peritoneal disseminated ovarian tumors.

Figure 3:
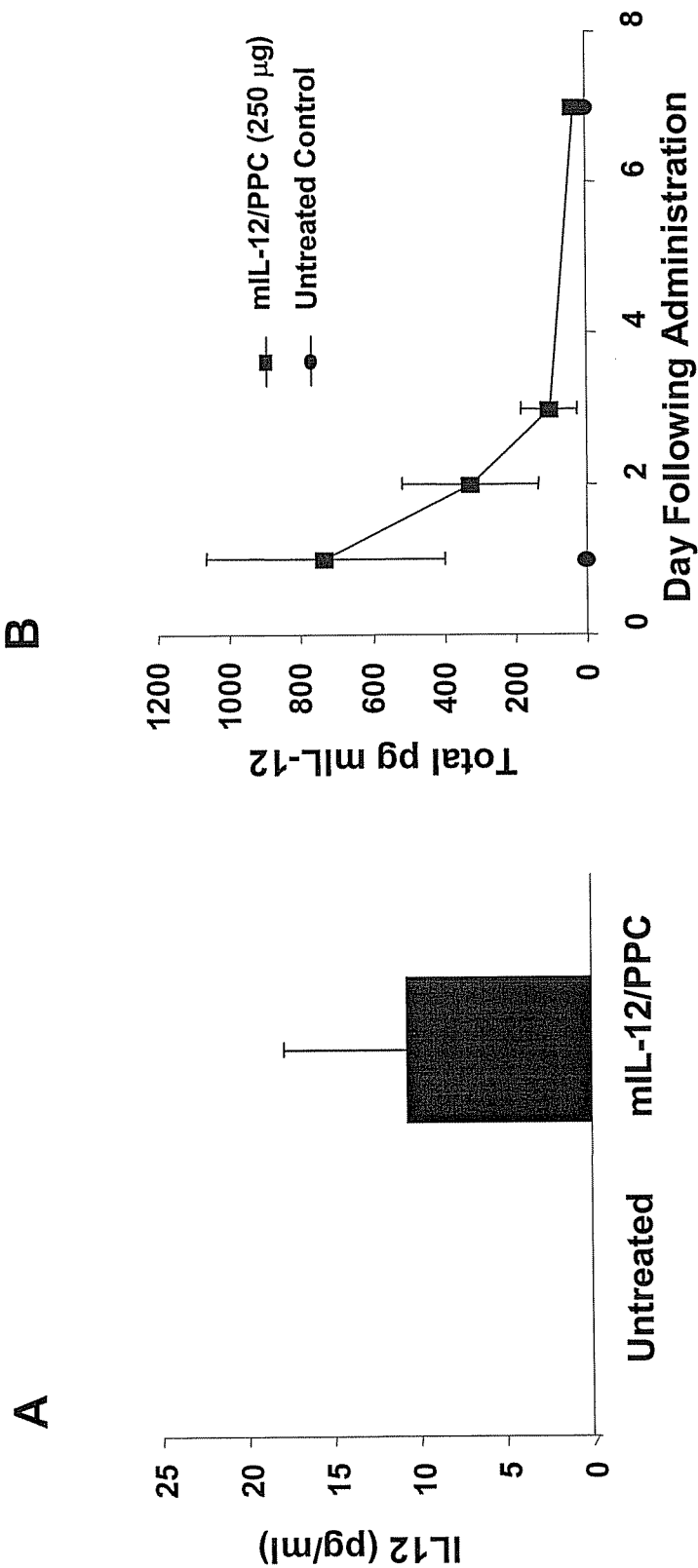
FIG. 3 illustrates IL-12 gene transfer into solid breast tumors by intratumoral administration (A) and into peritoneal disseminated ovarian tumors (ID8 tumors) by intraperitoneal injection (B) of pmIL-12/PPC complexes. PPC was complexed with a mouse IL-12 gene expression plasmid (pmIL-12), and administered intratumorally into 4T1 breast tumors and intraperitoneally into ID8 peritoneal tumor bearing mice. IL-12 levels were quantified after 24 hours in 4T1 tumors and after 1, 2, 3 and 7 days in the peritoneal ascites in ID8 tumor bearing animals.
Figure 4:
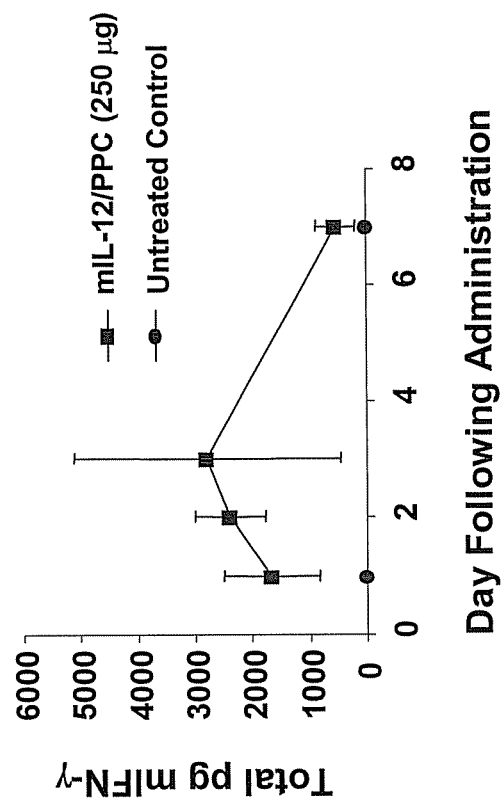
FIG. 4 illustrates the time course of IFN-$\gamma$ production following intraperitoneal administration of pmIL-12/PPC. PPC was complexed with a mouse IL-12 gene expression plasmid (pmIL-12), and administered intraperitoneal into ID8 peritoneal tumor bearing mice. IFN-$\gamma$ levels were quantified in peritoneal ascites after 1, 2, 3 and 7 days.

In both tumor models IL-12 gene transfer was manifested by an increase in IL-12 levels (FIG. 3). In peritoneal tumor bearing mice post-treatment IL-12 levels rose within 24 hours and declined to baseline level by 7 days. The kinetics of IL-12 action was closely related to a rise in IFN-γ, a downstream mediator of IL-12 actions (FIG. 4). The rise in IFN-γ levels was a bit delayed as expected and remained elevated above baseline after 7 days. These data demonstrate compositions comprising IL-12 expression plasmids and PPC are capable of manifesting IL-12 gene transfer in different tumor types and by different administration routes. The IL-12 gene transfer mediated by pmIL-12/PPC is therapeutically significant as it leads to a significant inhibition of tumor growth.

Figure 5:
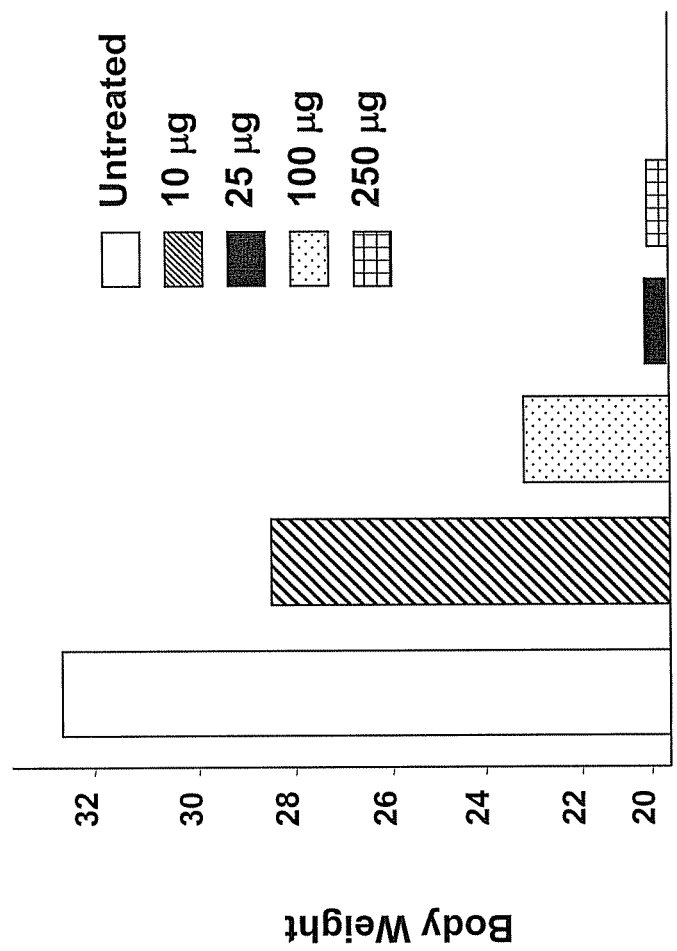
FIG. 5 illustrates dose-dependent inhibition of peritoneal disseminated ovarian tumors by intraperitoneal administration of pmIL-12/PPC complexes. pmIL-12/PPC complexes prepared at various DNA doses were administered intraperitoneally into peritoneal disseminated ID8 tumor bearing mice. The animals were periodically weighed to assess the effects of treatment on tumor burden, and survival data was recorded.
Figure 6:
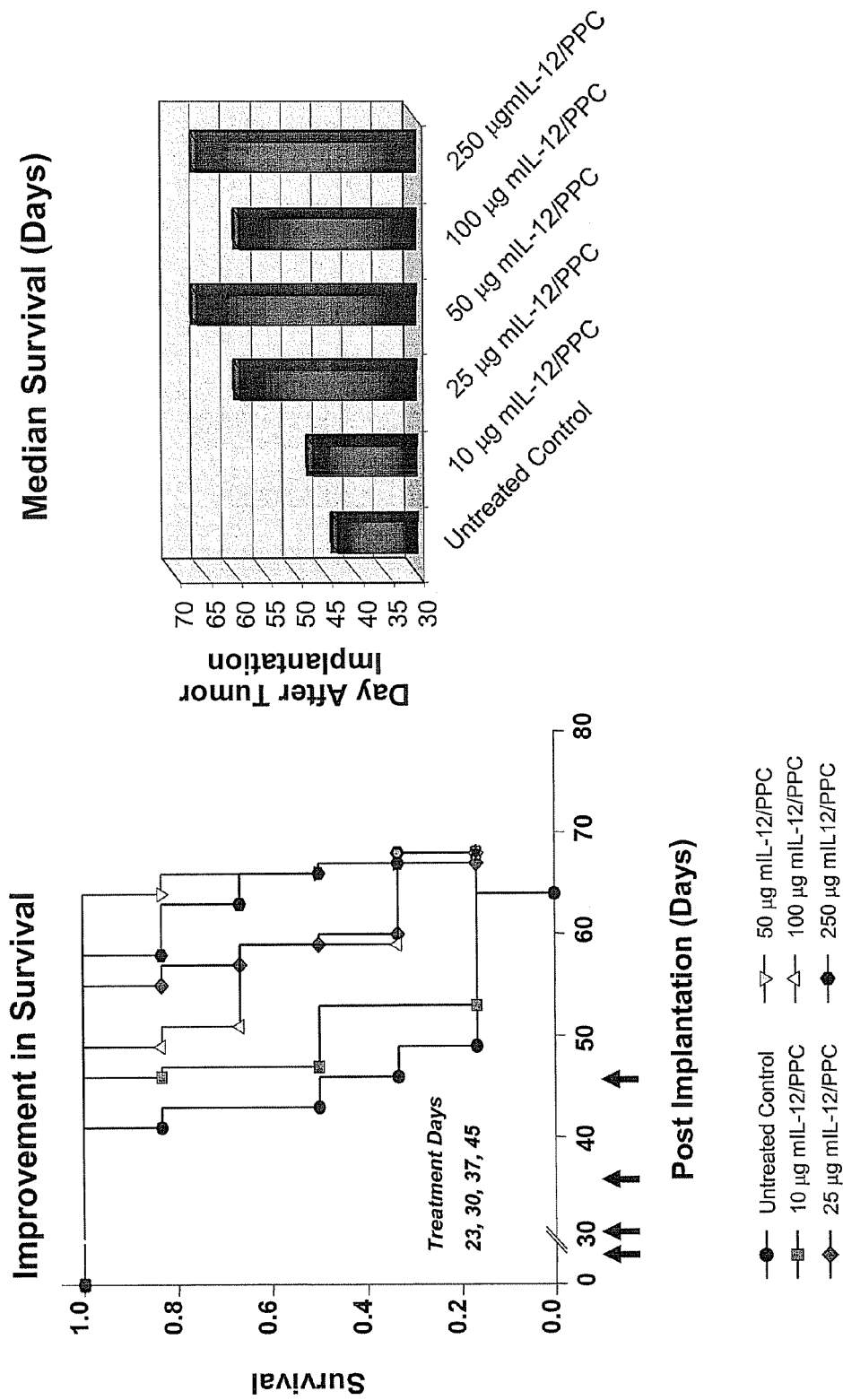
FIG. 6 illustrates improvement in the survival of peritoneal disseminated ovarian tumor bearing mice by intraperitoneal administration of pmIL-12/PPC complexes.
Figure 7:
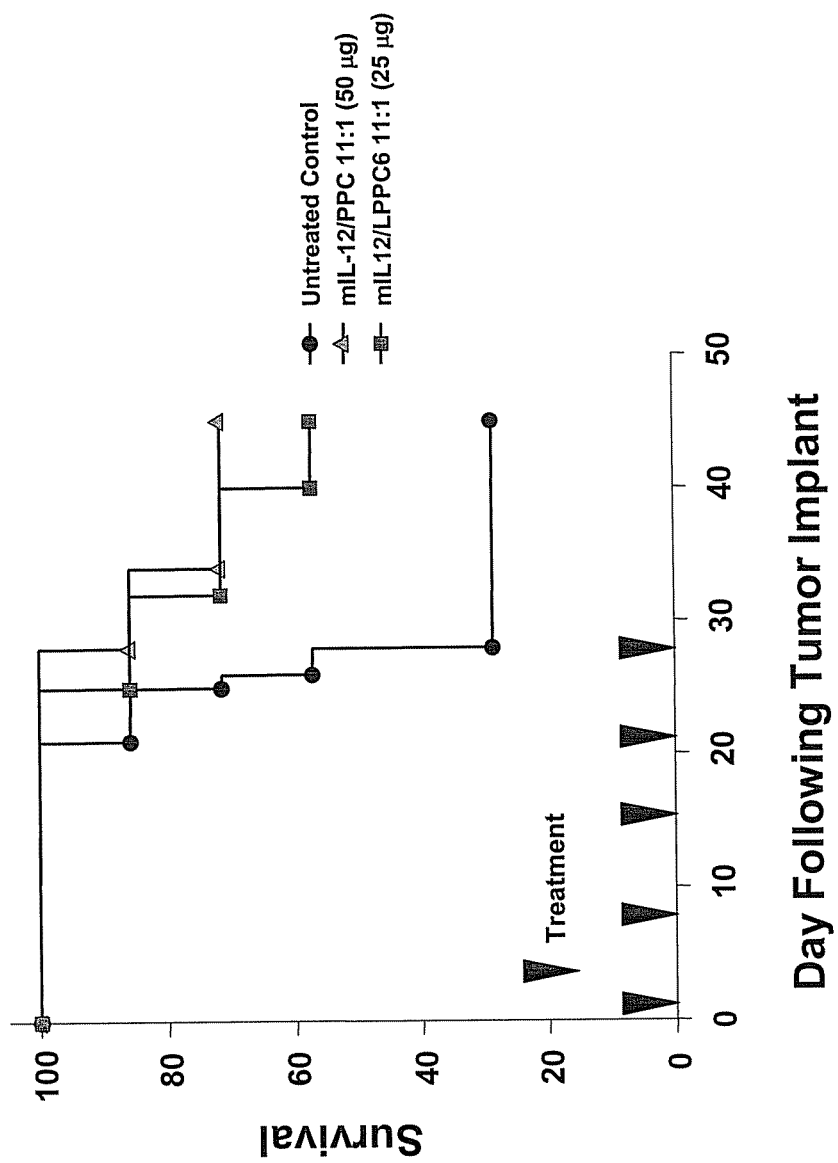
FIG. 7 illustrates improvement in the survival of peritoneal disseminated colorectal tumor bearing mice by intraperitoneal administration of pmIL-12/PPC complexes. pmIL-12/PPC complexes were administered intraperitoneally into the tumor bearing mice. The test and control animals were monitored for survival.
Figure 8:
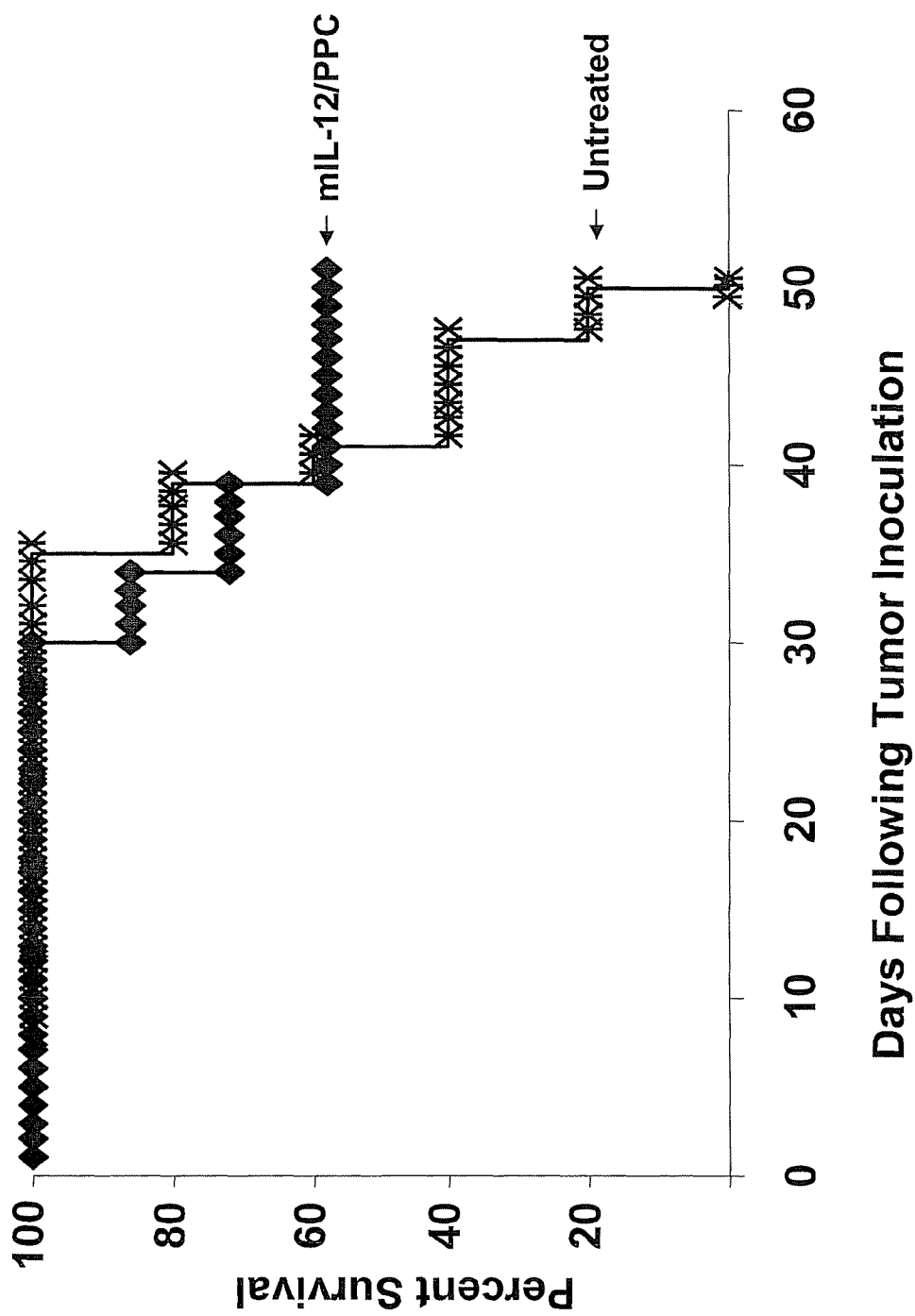
FIG. 8 illustrates improvement in the survival of GL-261 glioma bearing mice by intratumoral administration of pmIL-12/PPC complexes. pmIL-12/PPC complexes were administered into the cranial cavity at the time of tumor implantation. The test and control animals were monitored for survival.
Figure 9:
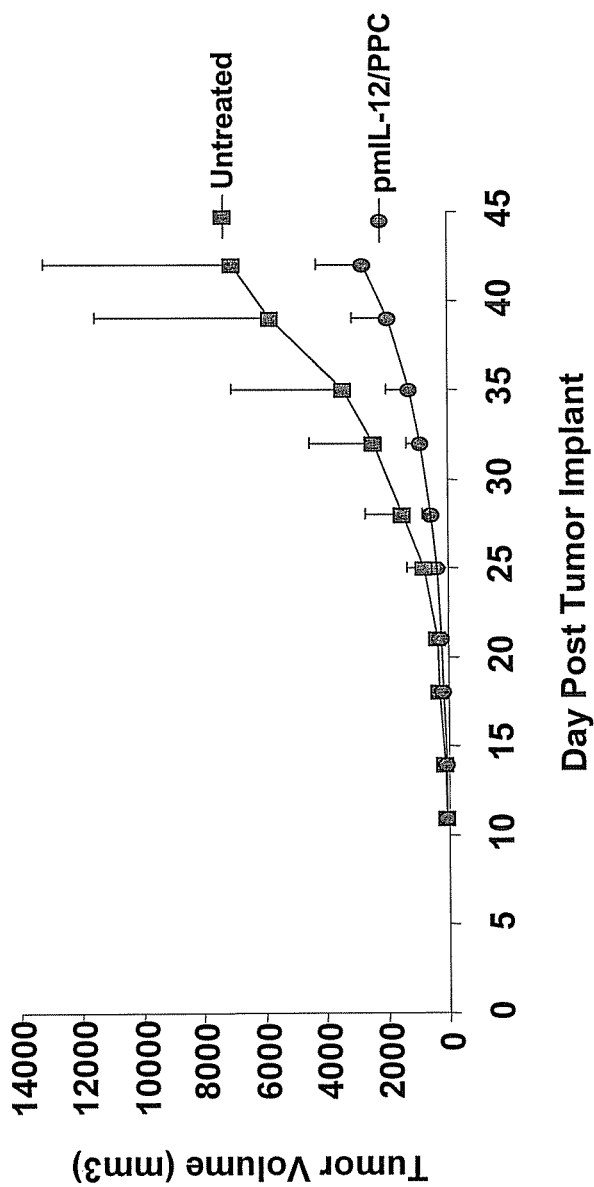
FIG. 9 illustrates inhibition of subcutaneous squamous cell carcinoma by intratumoral administration of pmIL-12/PPC complexes. The pmIL-12/PPC complexes were administered intratumorally into subcutaneous SCCVII tumors 6-7 days after tumor implantation and the treatment was repeated once every week for a total of 4 weeks. To assess the treatment efficacy, tumor size was measured periodically.

In mice with peritoneal disseminated ovarian tumors, intraperitoneal administration of pmIL-12/PPC complexes (N:P ratio 11:1) at a DNA dose of 10-250 μg significantly reduced the tumor burden (FIG. 5) and improved survival (FIG. 6) in a dose dependent manner. The therapeutic effect of pmIL-12/PPC (N:P ratio 11:1) was also observed in colorectal cancer. Intraperitoneal administration of 25 μg of pmIL-12/PPC complexes in mice with peritoneal disseminated colorectal cancer significantly prolonged their survival compared to untreated animals (FIG. 7). The anticancer efficacy of IL-12 gene transfer by pmIL-12/PPC was also observed in solid tumors following intratumoral administration. FIG. 8 illustrates the effects of intratumoral injection of pmIL-12/PPC on the growth of GL261 brain tumors. Treatment of intracranial implants of mouse GL261 glioma by local delivery of pIL-12/PPC complexes (N:P ratio 11:1) significantly enhanced survival. In mice with subcutaneously implanted squamous cell carcinoma of the head and neck, intratumoral administration of pmIL-12/PPC complexes once every week for four weeks produced a significant inhibition of the rate of tumor growth (FIG. 9). The anticancer effect of pmIL-12/PPC complexes was also observed in ovarian and breast tumors.

The composition of the present invention (nucleic acid and gene delivery polymer) does not exert adverse side effects when administered in vivo. For example, no compound related deaths or clinical signs of toxicity were associated with pmIL-12/PPC administration, intraperitoneally or subcutaneously. pmIL-12/PPC was well tolerated in both male and female mice at doses of 10, 50 and 250 μg per animal. Histopathologic examination of animals in both the IP and SC dose groups demonstrated no evidence of systemic toxicity due to pmIL-12/PPC, mild inflammation was noted in organs located in or adjacent to the injection site but which subsided during a one month recovery period. These results demonstrate that nucleic acid/polymer compositions for treatment of cancer are effective against a wide variety of cancers when given by different modes of administration and that repetitive in vivo delivery does not cause serious toxicity.

It is widely recognized that a single treatment strategy against cancer is generally ineffective due to the multi-factorial nature of this disease. The benefit of combination of more than one drug to maximize anticancer response is being increasingly recognized. Despite encouraging preclinical data the clinical success of the chemo-chemo combinations or chemo-cytokine combinations examined to date have not been satisfactory due to the inherent toxicity of chemotherapeutic drugs and recombinant cytokine proteins. This warrants the need for a safer chemo-immunotherapy approach to curtail protein toxicity and improve efficacy. In the present invention we have combined a chemotherapeutic agent with gene delivery of an anticancer gene administered locally to the tumor site to improve treatment safety and efficacy. Combining safe and efficient local delivery of an anticancer gene with a standard chemotherapeutic agent will enhance anticancer response and patient survival without augmenting toxicity. This combination therapy will reduce the chemotherapy dose and increase tumor sensitivity to the chemotherapy. In this invention, it is demonstrated that pharmaceutical compositions comprising an anticancer gene complexed with a cationic gene delivery polymer, and at least one adjunctive chemotherapeutic drug is more effective than gene therapy or chemotherapy treatment administered alone. Furthermore, the combination therapy is effective against a wide variety of tumors when given by different routes of administration and does not augment toxicity over individual therapies.

Figure 10:
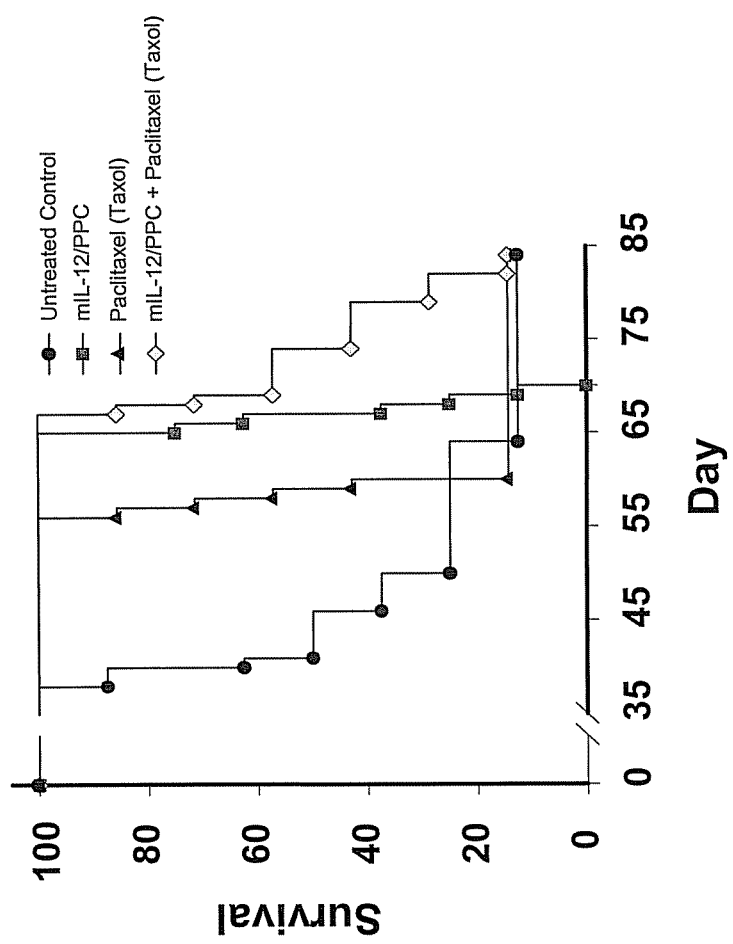
FIG. 10 illustrates inhibition of peritoneal disseminated ovarian tumors by combination therapy comprising intraperitoneal pmIL-12/PPC and intravenous paclitaxil. The pmIL-12/PPC complexes were administered by intraperitoneal injection 21 days after the implantation of tumor cells. The pmIL-12/PPC treatment was repeated 7 days later. Paclitaxel was administered intravenously only once, the day before the first gene injection. The test and control animals were monitored for survival.
Figure 11:
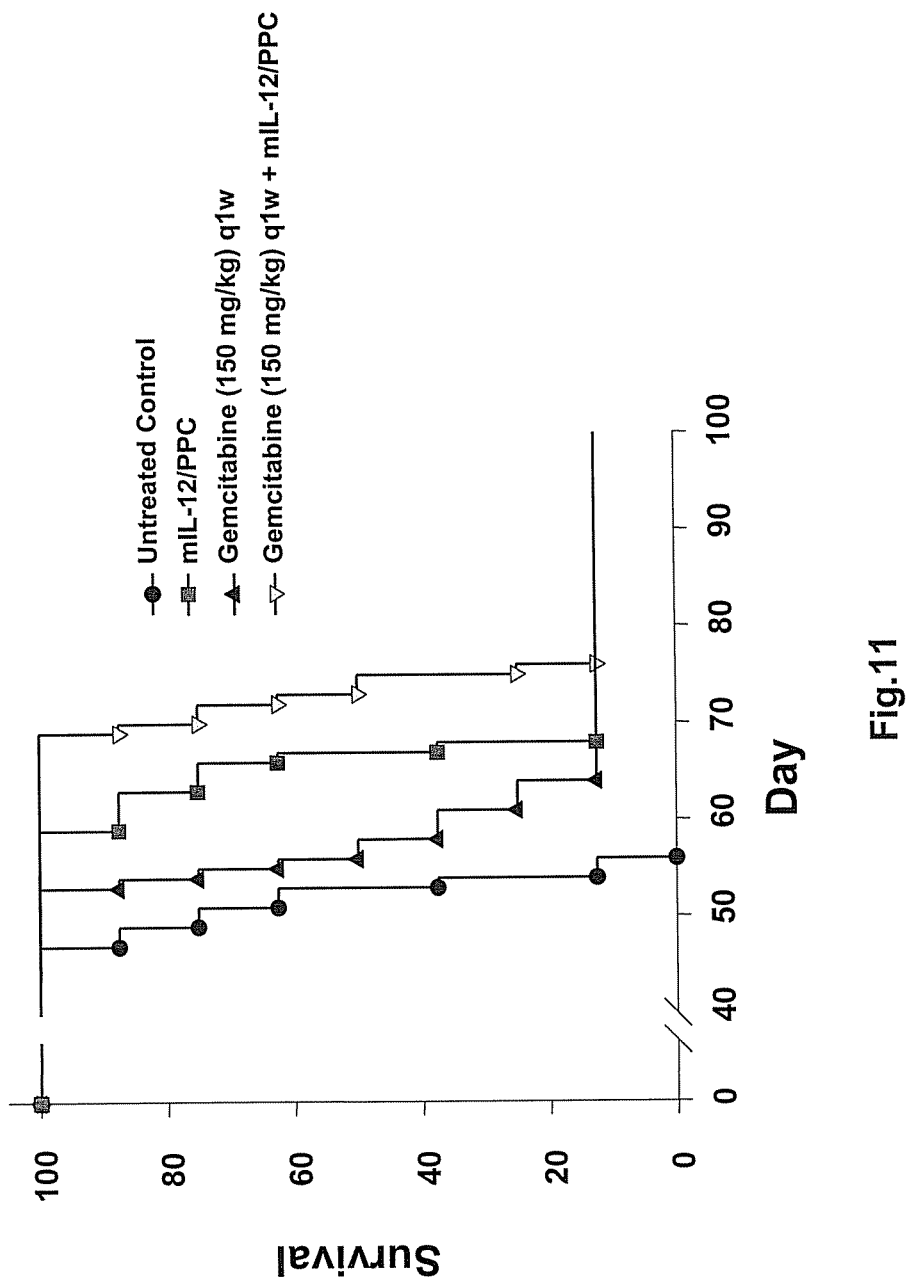
FIG. 11 illustrates inhibition of peritoneal disseminated ID8 ovarian tumors by combination therapy comprising intraperitoneal pmIL-12/PPC and gemcitabine chemotherapy. The tumor bearing mice were treated with intraperitoneal gemcitabine 14 days after tumor implantation and the treatment was repeated once every week for a total of 4 treatments. The first pmIL-12/PPC treatment was given 17 days after tumor implantation by intraperitoneal injection and repeated once every week for a total of 4 treatments. The test and control animals were monitored for survival.
Figure 12:
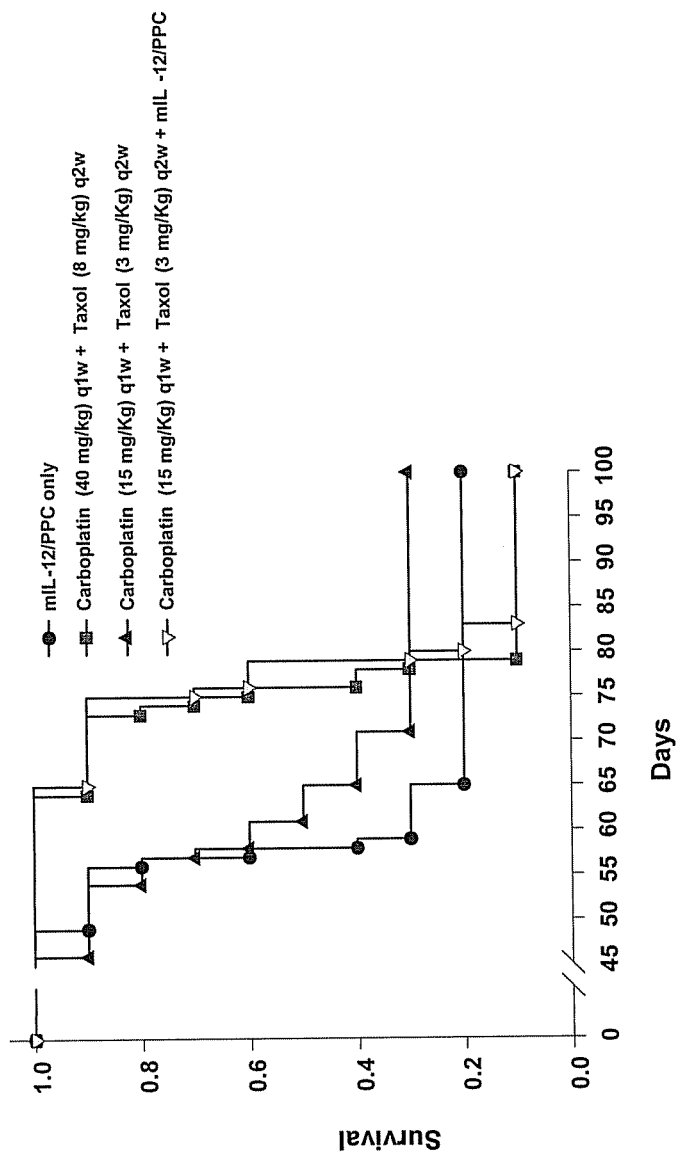
FIG. 12 illustrates inhibition of peritoneal disseminated ovarian tumors by combination therapy comprising intraperitoneal pmIL-12/PPC and carboplatin/paclitaxel chemotherapy. Chemotherapy treatment was started 15 days after tumor implantation, carboplatin was given once every week for 4 weeks and Taxol was given once every two week for a total of two treatments. The first pmIL-12/PPC treatment was given 18 days after tumor implantation by intraperitoneal injection and repeated once every week for a total of 4 treatments. The test and control animals were monitored for survival.

The anticancer response to combination therapy is demonstrated against ovarian tumors implanted into the peritoneal cavity. Intravenous administration of paclitaxil (Taxol®) (8 mg/Kg) or intraperitoneal administration of mIL-12 plasmid (25-100 μg)/PPC complexes (N:P ratio 11:1) produced tumor reduction and improved survival in tumor bearing mice. The pmIL-12/PPC treatment was more efficacious than the paclitaxel treatment. The combination IL-12 gene and paclitaxel therapy produced greater treatment response than the individual treatments (FIG. 10). A similar effect of the combination therapy on ovarian cancer was observed when IL-12 gene therapy was combined with another chemotherapeutic agent, gemcitabine (Gemzar®) (FIG. 11). The anti-cancer activity of gemcitabine was significantly enhanced when used alongside with the pmIL-12/PPC treatment. The combination of IL-12 gene therapy with a mixture of two chemotherapeutic agents was investigated. As shown in FIG. 12, combining IL-12 gene therapy with a carboplatin (Paraplatin®)/paclitaxel cocktail resulted in enhanced survival when compared to either IL-12 therapy alone or chemotherapy alone. Addition of IL-12 gene therapy to a suboptimal dose of carboplatin/paclitaxel enhanced the therapeutic efficacy similar to that achieved with a high chemotherapy dose (FIG. 12) without augmenting the toxicity.

Figure 13:
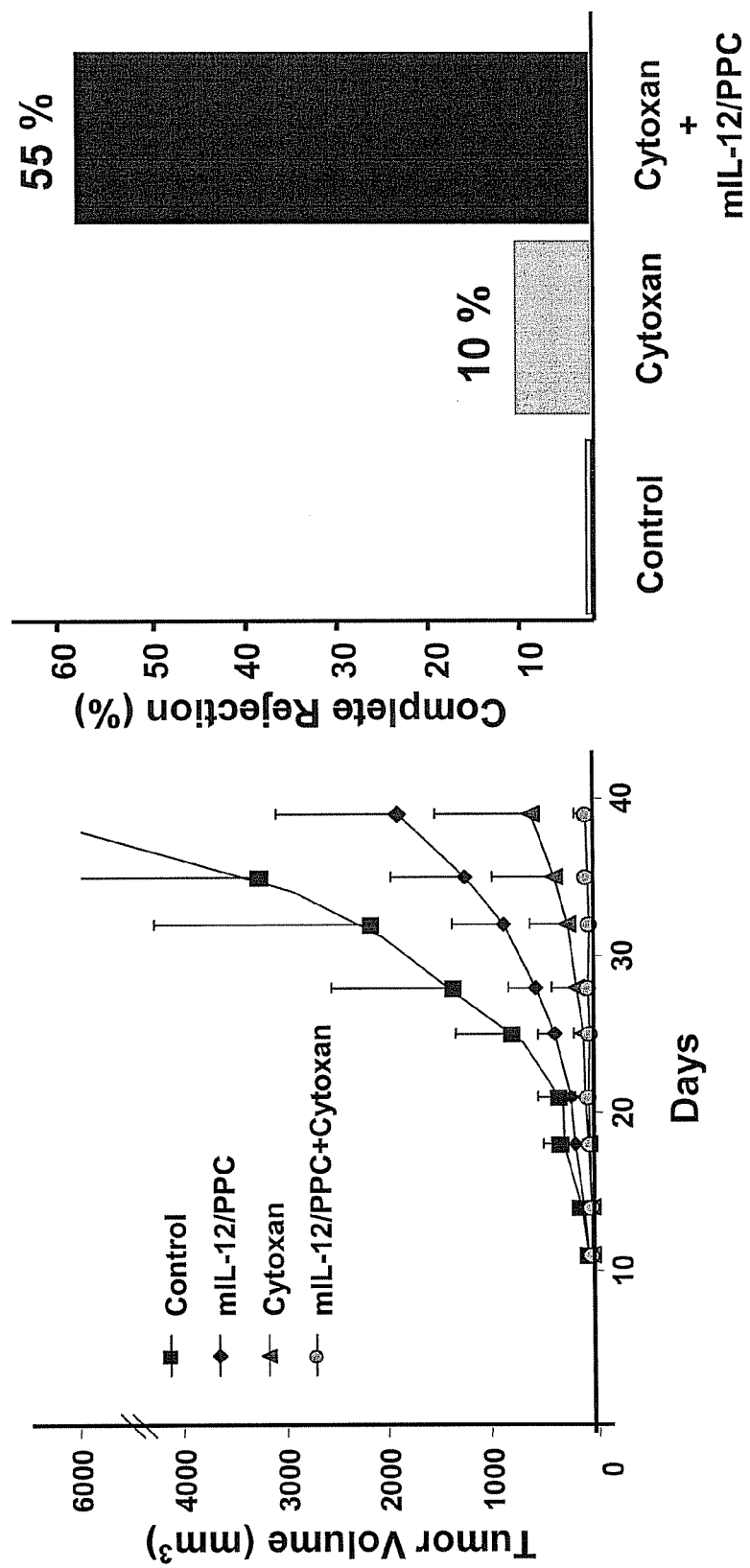
FIG. 13 illustrates inhibition of SCCVII tumors by intratumoral administration of pmIL-12/PPC complexes and cyclophosphamide chemotherapy. pmIL-12/PPC complexes were administered intratumorally into subcutaneous SCCVII tumors 6-7 days after tumor implantation and the treatment was repeated once every week for a total of 4 weeks. Cytoxan was administered intravenously one day before gene injection and repeated after 14 days. To assess treatment efficacy, tumor size was measured periodically.
Figure 14:
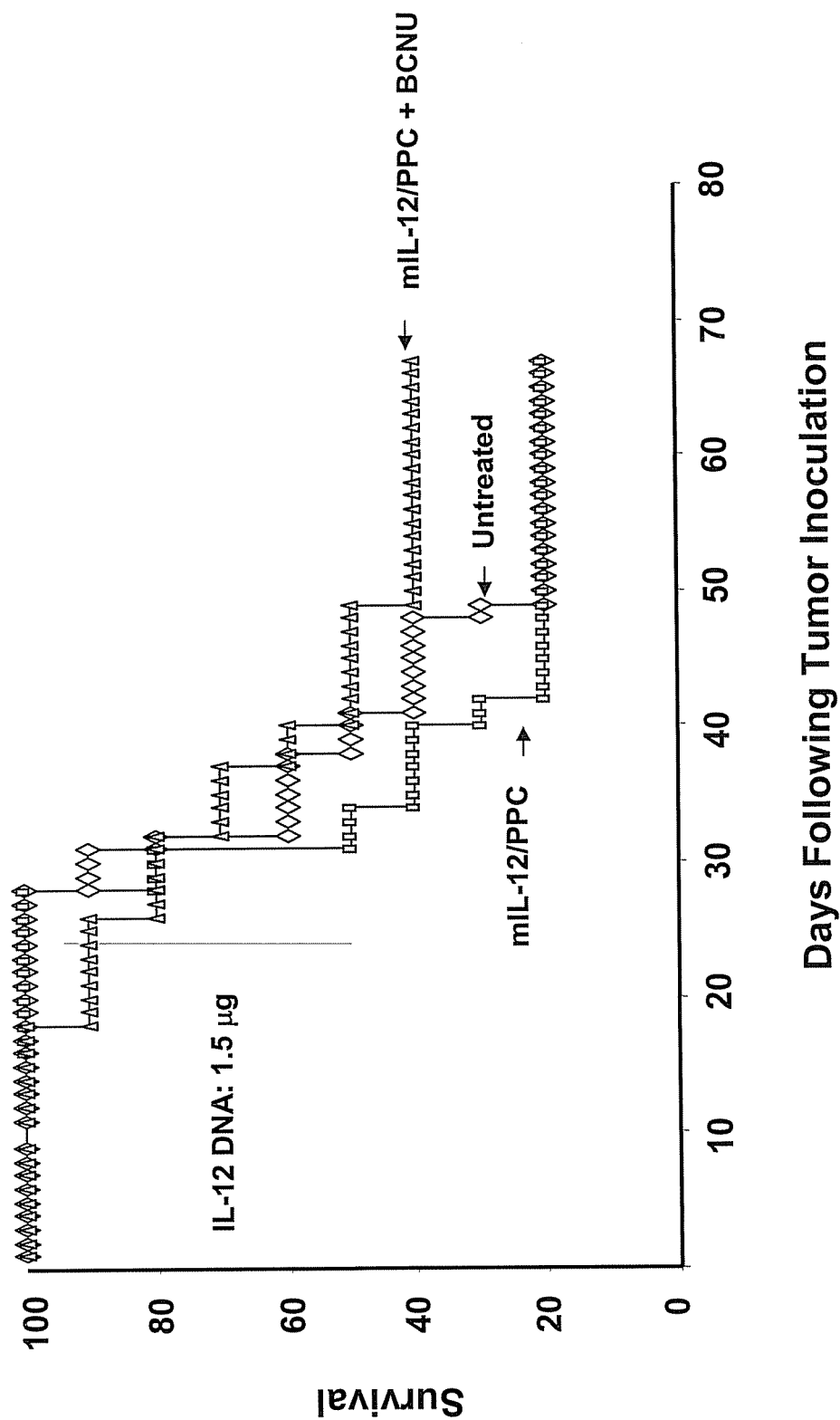
FIG. 14 illustrates inhibition of GL261 glioma by intratumoral administration of pmIL-12/PPC complexes and BCNU chemotherapy. pmIL-12/PPC complexes were administered into the cranial cavity at the time of tumor implantation. BCNU was administered as a Gliadel wafer 5 days after tumor implantation. The test and control animals were monitored for survival.

The improvement in anticancer response by combination therapy was also observed in solid tumors. For example in subcutaneous squamous cell carcinoma of the head and neck, intravenous administration of the chemotherapeutic agent cyclophosphamide (150 mg/kg) significantly reduced the tumor growth but did not completely inhibit it (FIG. 13). Intratumoral injection of pmIL-12/PPC alone caused about 30% inhibition of tumor growth. In contrast to the individual treatments, the cyclophosphamide plus pmIL-12/PPC combination treatment caused a complete inhibition of tumor growth. The complete rejection rate dramatically increased from only 10% with cyclophosphamide to 55% with cyclophosphamide plus pmIL-12/PPC complexes. A single intratumoral injection of a suboptimal dose (1.5 μg) of pmIL-12/PPC complexes in GL261 brain tumors did not significantly enhance the animal survival rate. However, combination of this suboptimal dose of pmIL-12/PPC with the chemotherapeutic agent BCNU (Gliadel® wafer) produced a significant enhancement in the survival rate (FIG. 14).

Figure 15:
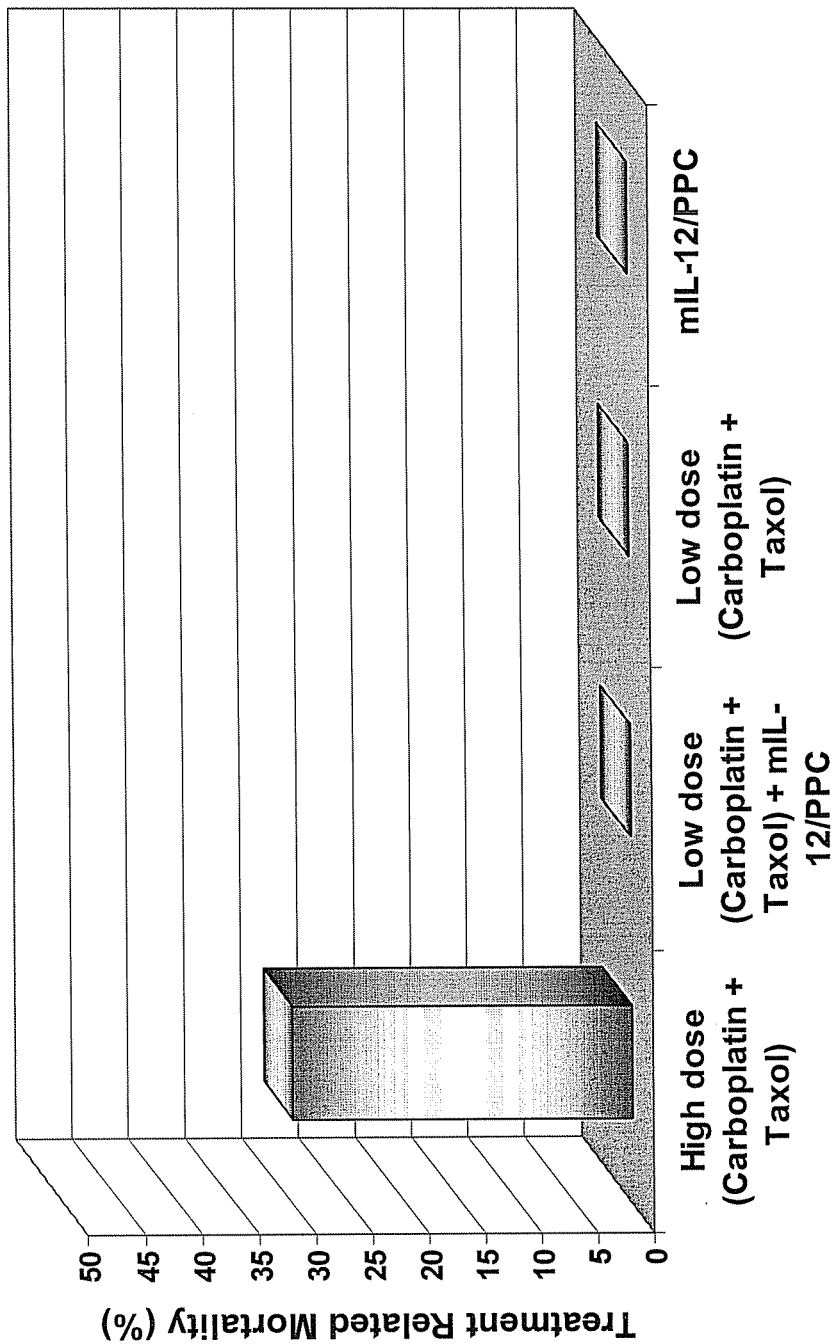
FIG. 15 illustrates that addition of IL-12/PPC gene therapy to low dose carboplatin/paclitaxel chemotherapy does not increase toxicity. In comparison, treatment with high dose carboplatin/paclitaxel chemotherapy led to a 30% rate of treatment-related deaths. Chemotherapy treatment was started 15 days after tumor implantation, carboplatin was given once every week for 4 weeks and Taxol was given once every two week for a total of two treatments. The first pmIL-12/PPC treatment was given 18 days after tumor implantation by intraperitoneal injection and repeated once every week for a total of 4 treatments. The entire treatment cycle was repeated three times. The test and control animals were monitored for survival.

Cancer treatment with high dose chemotherapy is associated with serious toxicity. To examine if the addition of IL-12/PPC to low dose chemotherapy augments treatment-related toxicity, peritoneal disseminated ovarian tumor-bearing mice were treated with three treatment cycles (as compared to single treatment cycle) of IL-12/PPC and low dose chemotherapy and monitored for signs of toxicity. Direct comparison was made with animals treated with three cycles of high dose chemotherapy treatment. As shown in FIG. 15, 50% of high dose chemotherapy group died due to treatment related toxicity (i.e., before reaching 40 gram) while none of IL-12/PPC+low dose chemotherapy group died from treatment toxicity. These results demonstrate that the toxicity of conventional chemotherapy (high dose) for cancer can be significantly reduced by lowering the chemotherapy dose and adding safer and efficacious IL-12 gene therapy.

These data demonstrate the anticancer efficacy of the said compositions comprising IL-12 plasmids and a novel gene delivery polymer, and its augmentation with a single or a mixture of chemotherapeutic agents. The combination approach provides a method by which the efficacy of a suboptimal dose of a chemotherapy regimen is enhanced without increasing toxicity.

The following examples will enable those skilled in the art to more clearly understand how to practice the present invention. It is to be understood that, while the invention has been described in conjunction with the preferred specific embodiments thereof, that which follows is intended to illustrate and not limit the scope of the invention. Other aspects of the invention will be apparent to those skilled in the art to which the invention pertains.

Example 1

IL-12 Gene Transfer into Peritoneal Disseminated or Subcutaneous Tumors by Local Administration of pIL-12/PPC Complexes The ability of local delivery of pIL-12/PPC complexes to produce IL-12 levels in subcutaneous and peritoneal disseminated tumor bearing mice was examined. For subcutaneous tumor studies, female BALB/c mice (7 weeks, 14-18 grams) mice were injected subcutaneously (sc) in the left and right flanks, with $1 \times 10^6$ 4T1 cells each. After the tumors had reached an approximate tumor size of 60 mm$^3$ they were injected with pmIL-12/PPC complexes containing 6 µg of DNA. The mice were sacrificed 24 hours later and their tumors harvested for mIL12 analysis by ELISA. The mIL-12 levels in tumors 24 hours after the injection are shown in FIG. 3A.

For peritoneal tumor studies, female C57/BL6 mice were injected intraperitoneally (ip) with $5 \times 10^6$ ID8 cells in a volume of 500 µl. The treatments were started when the tumor burden (mouse weight) reached approximately 20 grams (~21 days after injection of cells). The mice were injected intraperitoneally with a single dose of pmIL-12/PPC at a 11:1 nitrogen (N) to phosphate (P) ratio (N:P ratio) in a volume of 500 µl. Ascites fluid was removed from the tumor bearing animals 1, 2, 3 and 7 days after the mice had been treated with pmIL-12/PPC. Levels of mIL-12 and IFN-γ, were determined by ELISA and normalized to total ascitic fluid. The results show that significant levels of mIL-12 are seen in ascites fluid with peak levels achieved 1 day after treatment with levels falling to near base line by 7 days after treatment (FIG. 3B). Levels of IFN-γ are similarly seen to rise but peak levels are temporarily delayed (day 3 peak) with respect to IL-12 levels and by 7 days after treatment had fallen but were still significantly above baseline levels (FIG. 4).

Example 2

Treatment of Peritoneal Disseminated Ovarian Tumors by Intraperitoneal Administration of pIL-12/PPC Complexes Mice were injected intraperitoneally with $5 \times 10^6$ ID8 cells at a volume of 500 µl. The treatments were started when the tumor burden (mouse weight) reached approximately 20 grams (~21 days after injection of the cells). The mice were injected intraperitoneally with three weekly injections of 10-250 µg of pIL-12 complexed with PPC at a 11:1 N:P ratio in a volume of 500 µl. The mice were periodically weighed during the course of the study. Weight gain is predominantly caused by ascites accumulation which provides an indirect assessment of disease progression and tumor burden. The pmIL-12/PPC treatment produced a dose dependent inhibition of the tumor burden (FIG. 5) and prolongation of animal survival (FIG. 6).

Example 3

Treatment of Peritoneal Disseminated Colorectal Tumors by Intraperitoneal Administration of pIL-12/PPC Complexes Mice were injected intraperitoneally with $0.1 \times 10^6$ CT26 cells in a volume of 500 µl. The treatments were started 1 day after tumor implantation. The mice were injected intraperitoneally with five weekly injections of 50 µg of pmIL-12 complexed with PPC or 25 µg of pIL-12 complexed with LPPC6 at an 11:1 N:P ratio in a volume of 500 µl. LPPC6 is a linear polyethylenimine of 15 kD to which one molecule of mPEG and 6 molecules of cholesterol are independently attached. As illustrated in FIG. 7, the pmIL-12/PPC and pmIL-12/LPPC6 treatment produced a significant improvement in survival over untreated controls in this highly aggressive tumor model.

Example 4

Treatment of Brain Cancer by Intratumoral Administration of pIL-12/PPC Complexes.

The effect of local delivery of pmIL-12/PPC complexes was examined in a mouse glioma model. Tumors were implanted in the cerebral cortex of mice by intracranial injection of $1 \times 10^5$ GL261 glioma cells together with the co-injection of pmIL-12/PPC complexes. The animals were monitored for any sign of neurotoxicity and autopsied, when possible, to confirm that death was due to the intracranial tumor. Survival was plotted using a Kaplan-Meier survival analysis. A single intracranial injection of pmIL-12/PPC complexes administered at a dose range of 2.5-30 µg of plasmid was well tolerated as no significant adverse effects were observed. A single injection of pmIL-12/PPC complexes at a dose of 15 ug plasmid produced a significant enhancement in animal survival (FIG. 8).

Example 5

Treatment of Head & Neck Cancer by Intratumoral Administration of pIL-12/PPC Complexes The effect of local administration of pIL-12/PPC complexes on the growth of subcutaneously implanted squamous cell (SCCVII) carcinoma was examined. $4 \times 10^5$ squamous carcinoma cells in 100 µl were implanted sc on the right flank of female Female CH3 mice (6-9 weeks, 17-22 grams) The mIL-12 plasmid was complexed with PPC at a 11:1 N:P ratio and administered locally into the tumors at a DNA dose of 25 µg in an injection volume of 50 µl once every week for four weeks starting ~11 days after tumor implantation. Treatment groups of 12 mice were used and tumor growth was monitored twice per week using calliper measurement. As shown in FIG. 9, intratumoral administration of pmIL-12/PPC complexes produced a partial but significant inhibition of tumor growth.

Example 6 pIL-12/PPC Plus Paclitaxel Combination Therapy for the Treatment of Peritoneal Disseminated Ovarian Tumors Intraperitoneal IL-12 gene therapy was combined with paclitaxel chemotherapy to enhance the therapeutic response to disseminated ovarian tumors in mice. The mice were injected intraperitoneally with $5\times10^6$ ID8 cells in a volume of 500 µl. The treatments were started when tumor burden (mouse weight) reached approximately 20 grams (~21 days after injection of cells). The mice were injected intraperitoneally with 25 µg of pmIL-12 complexed with PPC at a 11:1 N:P ratio in a volume of 500 µl. The gene treatment was repeated after 7 days constituting a total of two injections (Day 1, 8) per the study. Paclitaxel (Taxol®) was administered only once (Day 0) by intravenous injection at a dose of 8 mg/kg dose in an injection volume of 250 µL. For combination therapy, both gene therapy and chemotherapy treatments were given as described above. Animals were periodically weighed to assess the effect of gene treatment on tumor burden. Intraperitoneal injection of pmIL-12/PPC complexes alone produced significant reduction of peritoneal tumor burden. The inhibition of tumor burden by pmIL-12/PPC complexes was slightly higher than that of paclitaxel. Addition of IL-12 gene therapy to paclitaxel resulted in an improvement in paclitaxil action on tumor burden and survival (FIG. 10).

Example 7 pIL-12/PPC Plus Gemcitabine Combination Therapy for the Treatment of Peritoneal Disseminated Ovarian Cancer The efficacy of combining IL-12 gene therapy with Gemcitabine (Gemzar®) was evaluated. Gemcitabine belongs to a general group of chemotherapy drugs known as antimetabolites. It is used to treat pancreatic cancer, breast cancer (along with paclitaxel), and lung cancer (along with cisplatin), and is currently being evaluated clinically for use against ovarian cancer. For this study, mice (C57BL/6) were injected intraperitoneally with $2.5\times10^6$ ID8 cells in a volume of 500 µl to induce disseminated tumor formation. At 14 days after tumor implantation gemcitabine was administered intraperitoneally at a dose of 150 mg/kg in a volume of 250 µl. Treatment was repeated weekly for a total of 4 treatments. Starting 17 days after tumor implantation, selected groups of mice were treated intraperitoneally with 25 µg of IL-12 plasmids complexed with PPC at a 11:1 N:P ratio in a volume of 500 µl. Plasmid administration was repeated weekly for a total of four treatments. Combination treatment of IL-12 gene therapy and gemcitabine chemotherapy significantly improved survival compared to either monotherapy alone (FIG. 11).

Example 8

PIL-12/PPC Plus Carboplatin/Paclitaxel Combination Therapy for the Treatment of Peritoneal Disseminated Ovarian Cancer Frontline chemotherapy for ovarian cancer continues to be a platinum agent (carboplatin, cisplatin) and paclitaxel. Thus, we were interested in evaluating the use of IL-12 gene therapy in combination with a carboplatin/paclitaxel chemotherapy regimen. Mice (C57BL/6) were injected intraperitoneally with $2.5\times10^6$ ID8 cells in a volume of 500 µl. Chemotherapy treatment was started 15 days after tumor implantation. Carboplatin (Paraplatin®) administration was at either 40 mg/kg ip in 250 ml (high dose) or 15 mg/kg in 250 µl (low dose) and paclitaxel (Taxol®) administration was given at either 8 mg/kg ip in 250 µl (high dose) or 3 mg/kg intraperitoneally in 250 ml (low dose). Carboplatin was give once weekly for a total of 4 treatments and paclitaxel was given q2w for a total of two treatments. When carboplatin and paclitaxel were given on the same day the paclitaxel was administered first and then carboplatin two hours later. Starting 18 days after tumor implantation, mice in selected groups were treated intraperitoneally with 25 µg of IL-12 plasmid complexed with PPC at a 11:1 N:P ratio in a volume of 500 µl. Plasmid administration was repeated weekly for a total of four treatments. Following the end of the treatment regimen the animals were monitored for survival. The results indicate that both the IL-12 gene therapy and the low dose carboplatin/paclitaxel chemotherapy produced similar survival outcomes (FIG. 12). In contrast when low dose chemotherapy was combined with IL-12 gene therapy the efficacy improved to a level that was nearly identical to that of the high dose chemotherapy treatment regimen. It would be advantageous to be able to use IL-12 gene therapy in combination with low dose chemotherapy in order to maintain therapeutic efficacy while using lower chemotherapy doses in order to minimize toxicities. This would potentially allow patients to remain on chemotherapy treatment regimens for prolonged periods of time offering the chance for a greatly enhanced therapeutic response.

Example 9 pIL-12/PPC Plus Cyclophosphamide Combination Therapy for the Treatment of Head and Neck Cancer Intratumoral IL-12 gene therapy was combined with cyclophosphamide (Cytoxan®) chemotherapy to enhance the therapeutic response in head and neck cancer. $4\times10^5$ squamous carcinoma cells (SCCVII) in 100 µl were implanted sc on the right flank of female Female CH3 mice (6-9 weeks, 17-22 grams). Five days prior to cyclophosphamide treatment (approximately 11 days after tumor implant) mIL-12 plasmids were complexed with PPC at a 11:1 N:P ratio and administered locally into the tumors at a DNA dose of 25 µg in an injection volume of 50 µl once every week for four weeks. Cyclophosphamide therapy was administered intravenously at a dose of 200 mg/kg in an injection volume of 125 µl alone or in combination with pIL-12 gene therapy. Cyclophosphamide treatment was repeated after 14 days constituting a total of two injections per study. For combination therapy both gene therapy and chemotherapy treatment were given as described above. Treatment groups of 12 mice were used and tumor growth was monitored twice per week using calliper measurement. As shown in FIG. 13, intratumoral administration of pmIL-12/PPC complexes or intravenous injection of cyclophosphamide alone produced only a partial inhibition of tumor growth while their combination produced complete inhibition. There was a higher percentage of animals treated with combination therapy that completely rejected the tumor (55%) as opposed to the animals treated with chemotherapy alone (10%).

Example 10

Treatment of Brain Cancer by Intratumoral pIL-12/PPC and BCNU Combination Therapy.

The effect of local delivery of pmIL-12/PPC complexes alone or in combination with BCNU (Gliadel®) was examined in a mouse glioma model. Gliadel® wafer is a polymeric formulation of carmustine or BCNU, a chemotherapeutic agent of the nitrosourea family. Tumors were implanted in the cerebral cortex of mice by intracranial injection of $1\times10^5$ GL261 glioma cells together with the co-injection of pmIL-12/PPC complexes. Five days after tumor implantation, Gliadel® containing 10% BCNU was implanted below the inner table of the parietal bone. Animals were monitored for any sign of neurotoxicity and autopsied, when possible, to confirm that death was due to intracranial tumor. Survival was plotted using a Kaplan-Meier survival analysis. A single intracranial injection of pmIL-12/PPC complexes administered in a dose range of 2.5-30 µg of plasmid was well tolerated as no significant adverse effects were observed. A single injection of pmIL-12/PPC complexes administered at a 1.5 ug plasmid dose did not increase the survival rate. However, combination of this suboptimal dose of pmIL-12/PPC with BCNU significantly enhanced survival (FIG. 14). The enhancement in survival from combination therapy was higher than historically achieved with BCNU alone in this model (data not shown).

Example 11

Comparison of Toxicity of IL-12/PPC Plus Low Dose Carboplatin/Paclitaxel Combination Therapy and High Dose Carboplatin/Paclitaxel Combination Therapy.

It has been previously demonstrated by the applicants that combining IL-12/PPC with low dose carboplatin (15 mg/kg) and paclitaxel (3 mg/kg) therapy produces anticancer efficacy similar to high dose carboplatin (40 mg/kg) and paclitaxel (8 mg/kg) chemotherapy (Example 8, FIG. 12). In this example, it is examined if IL-12/PPC plus low dose combination chemotherapy is less toxic than the high dose chemotherapy. Mice bearing peritoneal disseminated ovarian tumors were administered with three treatment cycles of IL-12/PPC+low dose chemotherapy or high dose chemotherapy as compared to only one treatment cycle used in the previous examples. Animal mortality occurring prior to reaching the 40 gram body weight cut-off (criterion for sacrificing animals due to disease advancement) and not showing significant tumor burden at necropsy were considered treatment related. Mice (C57BL/6) were injected intraperitoneally with $2.5 \times 10^6$ ID8 cells in a volume of 500 µl. Chemotherapy treatment was started 15 days after tumor implantation. Carboplatin (Paraplatin®) administration was at either 40 mg/kg ip in 250 ml (high dose) or 15 mg/kg in 250 µl (low dose) and paclitaxel (Taxol®) administration was given at either 8 mg/kg ip in 250 µl (high dose) or 3 mg/kg intraperitoneally in 250 ml (low dose). Carboplatin was give once weekly for a total of 4 treatments and paclitaxel was given q2w for a total of two treatments. On treatment days paclitaxel was administered first and then carboplatin two hours later. Starting 18 days after tumor implantation, mice in selected groups were treated intraperitoneally with 100 µg of IL-12 plasmid complexed with PPC at a 11:1 N:P ratio in a volume of 500 µl. Plasmid administration was repeated weekly for a total of four treatments. The entire treatment cycle was repeated three times (12 weeks total), and the animals were monitored for survival. As shown in FIG. 15, 30% of high dose chemotherapy group died due to treatment related toxicity (i.e., before reaching 40 gram) compared to 0% treatment related death in IL-12/PPC+low dose chemotherapy group, in the low dose chemotherapy group or the IL-12/PPC only treatment group. These results demonstrate that in comparison to a high dose chemotherapy regimen, combining IL-12/PPC with low dose chemotherapy produces relatively fewer treatment related deaths but produces similar anticancer efficacy (FIG. 12).

It is to be understood that the above-described embodiments are only illustrative of the application of the principles of the present invention. Numerous modifications and alternative embodiments can be derived without departing from the spirit and scope of the present invention and the appended claims are intended to cover such modifications and arrangements. Thus, while the present invention has been shown in the drawings and is fully described above with particularity and detail in connection with what is presently deemed to be the most practical and preferred embodiment(s) of the invention, it will be apparent to those of ordinary skill in the art that numerous modifications can be made without departing from the principles and concepts of the invention.

We claim:

1. A method of treating a hyperproliferative disorder in a subject in need thereof comprising administering a pharmaceutical composition comprising: (1) a DNA plasmid that encodes an anti-proliferative molecule selected from the group consisting of interleukin-2, interleukin-4, interleukin-7, IL-15, interferon-α, interferon-β, interferon-γ, colony stimulating factor, granulocyte-macrophage colony stimulating factor, anti-proliferative anti-angiogenic agents, TNF-α, eNOS, iNOS, IP10, p16, thymidine kinase, p53, Fas-ligand, anti-proliferative bacterial antigens, anti-proliferative viral antigens, anti-proliferative tumor antigens and any combination thereof; and (2) a lipopolymer, wherein the lipopolymer comprises a polyethylenimine backbone, wherein cholesterol and polyethylene glycol are each covalently linked to the polyethylenimine backbone; to the subject, wherein the anti-proliferative molecule is expressed in the subject such that a hyperproliferative disorder is treated.

2. The method of claim 1, further comprising administering at least one chemotherapeutic or anticancer agent to the subject.

3. The method of claim 1, wherein the hyperproliferative disorder is cancer.

4. The method of claim 1, wherein the pharmaceutical composition provides a systemic effect in the subject.

5. A method of delivering an anti-proliferative molecule to hyperproliferative cells comprising contacting the hyperproliferative cells with a pharmaceutical composition comprising (1) a DNA plasmid that encodes an anti-proliferative molecule selected from the group consisting of interleukin-2, interleukin-4, interleukin-7, IL-15, interferon-α, interferon-β, interferon-γ, colony stimulating factor, granulocyte-macrophage colony stimulating factor, anti-proliferative anti-angiogenic agents, TNF-α, eNOS, iNOS, IP10, p16, thymidine kinase, p53, Fas-ligand, anti-proliferative bacterial antigens, anti-proliferative viral antigens, anti-proliferative tumor antigens and any combination thereof and (2) a lipopolymer, wherein the lipopolymer comprises a polyethylenimine backbone, wherein cholesterol and polyethylene glycol are each covalently linked to the polyethylenimine backbone, wherein the anti-proliferative molecule is expressed in the hyperproliferative cells resulting in a decrease of proliferation of the hyperproliferative cells.

6. The method of claim 5, further comprising administering at least one chemotherapeutic or anticancer agent to the hyperproliferative cells.

7. The method of claim 1, wherein the anti-proliferative molecule is a protein or an shRNA.

8. The method of claim 7, wherein the anti-proliferative protein is a cytokine.

9. The method of claim 1, wherein the polyethylenimine backbone has a linear or branch configuration with a molecular weight of 100-500,000 Daltons.

10. The method of claim 1, wherein the cholesterol is attached to the polyethylenimine backbone through a polyethylene glycol spacer.

11. The method of claim 1, wherein the polyethylene glycol has molecular weight of between 50 to 20,000 Daltons.

12. The method of claim 1, wherein the molar ratio of polyethylene glycol to polyethylenimine is within a range of 0.1:1 to 500:1.

13. The method of claim 1, wherein molar ratio of the cholesterol to polyethylenimine is within a range of 0.1:1 to 500:1.

14. The method of claim 1, wherein the polyethylenimine backbone further comprises a targeting moiety, wherein the targeting moiety is directly attached to the polyethylenimine backbone or is attached to the polyethylenimine backbone through a polyethylene glycol linker.

15. The method of claim 14, wherein the molar ratio of the lipopolymer to targeting moiety is within a range of 1:0.1 to 1:100.

16. The method of claim 1, wherein the DNA plasmid is complexed with the lipopolymer at nitrogen moles in the lipopolymer to phosphate moles in the plasmid DNA at a molar ratio of 0.1:100 to 100:1.

17. The method of claim 5, wherein the anti-proliferative molecule is a protein or an shRNA.

18. The method of claim 5, wherein the polyethylenimine backbone has a linear or branch configuration with a molecular weight of 100-500,000 Daltons.

19. The method of claim 5, wherein the cholesterol is attached to the polyethylenimine backbone through a polyethylene glycol spacer.

20. The method of claim 5, wherein the polyethylenimine backbone further comprises a targeting moiety, wherein the targeting moiety is directly attached to the polyethylenimine backbone or is attached to the polyethylenimine backbone through a polyethylene glycol linker.

* * * * *